(12) United States Patent
Takahashi

(10) Patent No.: US 8,569,453 B2
(45) Date of Patent: Oct. 29, 2013

(54) FLUORENE COMPOUND

(75) Inventor: Daisuke Takahashi, Mie (JP)

(73) Assignee: Ajinomoto Co., Inc., Tokyo (JP)

( * ) Notice: Subject to any disclaimer, the term of this patent is extended or adjusted under 35 U.S.C. 154(b) by 748 days.

(21) Appl. No.: 12/723,027

(22) Filed: Mar. 12, 2010

(65) Prior Publication Data

US 2010/0240867 A1 Sep. 23, 2010

Related U.S. Application Data

(60) Provisional application No. 61/159,998, filed on Mar. 13, 2009.

(30) Foreign Application Priority Data

Mar. 12, 2009 (JP) ................................. 2009-060291

(51) Int. Cl.
  *C07K 1/02* (2006.01)

(52) U.S. Cl.
  USPC .......................................... 530/338; 530/333

(58) Field of Classification Search
  None
  See application file for complete search history.

(56) References Cited

U.S. PATENT DOCUMENTS

| | | |
|---|---|---|
| 5,712,367 A | 1/1998 | Bernard et al. |
| 6,162,824 A | 12/2000 | Ognyanov et al. |
| 2007/0051922 A1 | 3/2007 | Nakatani et al. |

FOREIGN PATENT DOCUMENTS

| | | |
|---|---|---|
| JP | 2579699 B2 | 2/1997 |
| JP | 2003-44493 | 2/2000 |
| JP | 2005-126705 | 5/2005 |
| WO | WO 99/41227 | 8/1999 |
| WO | WO 2006/104166 A1 | 10/2006 |
| WO | WO 2007/034812 A1 | 3/2007 |
| WO | WO 2007/122847 A1 | 11/2007 |

OTHER PUBLICATIONS

Bleicher, Konrad and Wareing, James R.; "PhFl acetic acid: a new linker for solid phase organic synthesis." Tet. Let. (1998) 39 p. 4591-4594.*
Löhr, Birgit et al; "Modified trityl ester protecting groups in peptide synthesis." Synlett (1999) 7 p. 1136-1138.*
Hitoshi Tamiaki, et al., "A Novel Protecting Group for Constructing Combinatorial Peptide Libraries", The Chemical Society of Japan, 74, 2001, pp. 733-738.
Bernd Henkel, et al., "9-Hydroxy-9-(4-carboxyphenyl)fluorene—A New Linker for Solid Phase Synthesis)", Tetrahedron Levers, vol. 39, No. 51, 1998, pp. 9401-9402.
Konrad H. Bleicher, et al., "PhFl Acetic Acid: A New Linker for Solid Phase Organic Synthesis", Tetrahedron Letters, vol. 39, No. 26, 1998, pp. 4591-4594.
Yonggang Wu, et al., "Spiro-Bridged Ladder-Type Poly(p-phenylene)s: Towards Structurally Perfect Light-Emitting Materials", Journal of the American Chemical Society, vol. 130, No. 23, 2008, pp. 7192-7193.

* cited by examiner

*Primary Examiner* — Cecilia J Tsang
*Assistant Examiner* — Fred Reynolds
(74) *Attorney, Agent, or Firm* — Oblon, Spivak, McClelland, Maier & Neustadt, L.L.P.

(57) ABSTRACT

Particular compounds having a fluorene skeleton are superior in broad utility and stability, as a protecting reagent for liquid phase synthesis of amino acids and/or peptides.

4 Claims, No Drawings

SEQUENCE LISTING

```
<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Ser(tBu)
<220> FEATURE:
<221> NAME/KEY: MOD_RES
<222> LOCATION: (4)..(4)
<223> OTHER INFORMATION: Ala-O-fl

<400> SEQUENCE: 1

Ser Ile Pro Ala
1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Fmoc-Ser(tBu)

<400> SEQUENCE: 2

Ser Ile Pro Ala
1
```

FLUORENE COMPOUND

CROSS REFERENCES TO RELATED APPLICATIONS

This application claims priority to U.S. Provisional Patent Applications No. 61/159,998, filed on Mar. 13, 2009, and Japanese Patent Application No. 2009-060291, filed on Mar. 12, 2009, both of which are incorporated herein by reference in their entireties.

BACKGROUND OF THE INVENTION

1. Field of the Invention

The present invention relates to fluorene compounds which are useful as protecting reagents for organic synthesis reactions. The present invention also relates to organic synthesis reactions which use such a compound and the like. More particularly, the present invention relates to fluorene compounds which are usable as protecting reagents for a C-terminal and/or a side chain of amino acid or peptide in peptide synthesis, particularly liquid phase synthesis of a peptide, and methods of peptide synthesis and organic synthesis using such a compound.

2. Discussion of the Background

Methods for the organic synthesis of compounds are generally divided largely into solid phase methods and a liquid phase methods. The solid phase method is advantageous in that isolation and purification after the reaction can be performed by filtration and washing alone. However, the solid phase method is problematic in that it essentially includes a non-homogeneous phase reaction, reaction agents and reagents need to be used in excess amounts to compensate for the low reactivity, and tracking of reaction and analysis of the reaction product on a carrier are difficult.

In an attempt to perform reactions in a homogeneous liquid phase while utilizing the advantages of the solid phase method in that isolation and purification after the reaction can be performed by filtration and washing alone, a method of isolating a particular component dissolved in a liquid as a solid has been used. This is because precipitation of a particular component alone facilitates isolation and purification after reaction.

A particular component dissolved in a solution can be precipitated only when predetermined conditions, such as chemical properties, property and relationship with solvents of the compound, are satisfied.

However, determination of precipitation conditions requires trial and error and experimental searching in most cases. In liquid phase synthesis, moreover, some compounds to be synthesized are insoluble in organic solvents used for extraction or show low solubility therein, which necessitates confirmation of the property of each compound to search for isolation and purification methods therefor. Particularly, when sequential and multistep synthesis reactions are required as in peptide synthesis and the like, since isolation and purification conditions such as precipitation, extraction and the like need to be determined based on the properties unique to the compound synthesized in each step, a long time and high cost are required.

To solve such problems, a method using a carrier molecule wherein a dissolved state and an insolubilized state (precipitated state) irreversibly change according to the varying solvent composition has been developed. Using such a carrier, an isolation target compound can be selectively precipitated from a homogeneous solution state, in other words, a particular compound can be isolated after a liquid phase reaction when other soluble components still remain in a solution, thus obviating the need to consider extraction and precipitation conditions for each compound.

However, when a polymer is used as a carrier molecule, the reaction becomes non-homogeneous due to the molecular weight distribution, as in the solid phase method, where tracking of reaction and analysis of the reaction product on a carrier are difficult to perform, since the compound is bound to a carrier.

Thus, a method using a protecting group (anchor) capable of irreversible change from a dissolved state to an insolubilized state (precipitated state) of a particular component according to the varying solvent composition has been developed. For example, JP-A-2000-44493 and *Bull. Chem. Soc. Jpn.*, 74, 733-738 (2001) disclose methods including developing an anchor by introducing a long chain aliphatic group into a benzyl alcohol type compound (see the following structure), dissolving and reacting the anchor in a halogenated solvent, and precipitating a reacted product with methanol or acetonitrile to allow peptide chain elongation.

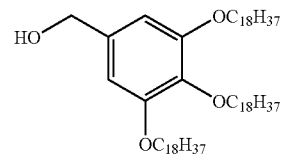

However, when the anchor is used for sequential reactions of peptide synthesis, deprotection of a second residue results in the production of the by-product diketopiperazine, which causes a sequence showing markedly decreased yield and peptide quality, thus posing problems in broad utility (particularly sequence containing proline). With such a benzyl type anchor, moreover, deprotection under strong acidic conditions is necessary, which prevents dissociation of a desired protecting group.

WO2007/122847 discloses a trityl type protecting group (see the following structure).

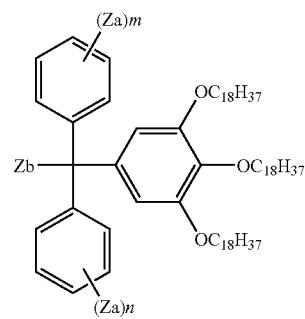

wherein m and n are each independently 0 or 1, Za is a chlorine atom or a bromine atom, and Zb is a hydroxyl group, a chlorine atom or a bromine atom.

With a protecting group of this trityl type, the formation of diketopiperazine as a by-product can be suppressed and selective deprotection can be performed. However, its property as a protecting group is too low, namely, the compound-anchor bond is easily cut and a decomposition reaction proceeds in which the anchor is dissociated even in methanol and the like. Therefore, the method is not satisfactory from the aspects of yield and quality.

SUMMARY OF THE INVENTION

Accordingly, it is one object of the present invention to provide novel compounds, which are superior in broad utility and stability, which are useful as a protecting group (anchor) for amino acid and/or peptide in liquid phase synthesis and the like of peptides.

It is another object of the present invention to provide novel organic synthesis reaction methods (particularly peptide liquid phase synthesis method) which employ such a compound.

It is another object of the present invention to provided novel kits for liquid phase synthesis of peptides, which contain such a compound.

It is another object of the present invention to provided novel intermediates which are useful for producing such a compound.

These and other objects, which will become apparent during the following detailed description, have been achieved by the inventors' discovery that a particular compound having a fluorene skeleton can solve the above-mentioned problems.

Accordingly, the present invention provides:is as described below.

(1) A fluorene compound represented by formula (I):

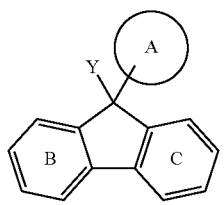

(I)

wherein ring A is an aromatic ring; Y is a group reactive with one or more kinds selected from an amino group, a carboxyl group and a mercapto group; at least one of rings A, B and C has an organic group having an aliphatic hydrocarbon group; and rings A, B and C each independently optionally have an electron-withdrawing group.

(2) A fluorene compound wherein 2 to 20 divalent unit structures derived from a compound represented by formula (I):

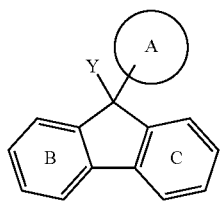

(I)

wherein ring A is an aromatic ring; Y is a group reactive with one or more kinds selected from an amino group, a carboxyl group and a mercapto group; at least one of rings A, B and C has an organic group having an aliphatic hydrocarbon group; and rings A, B and C each independently optionally have an electron-withdrawing group, are connected via an organic group having an aliphatic hydrocarbon group, which is contained in the unit structure.

(3) A fluorene compound represented by formula (I'):

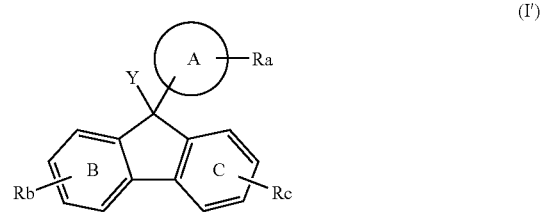

(I')

wherein ring A is an aromatic ring; Y is a group reactive with one or more kinds selected from an amino group, a carboxyl group and a mercapto group; Ra, Rb and Rc are each independently an organic group having an aliphatic hydrocarbon group, a hydrogen atom or an electron-withdrawing group, at least one of Ra, Rb and Rc is an organic group having an aliphatic hydrocarbon group; and rings A, B and C each independently optionally have an electron-withdrawing group.

(4) A fluorene compound represented by formula (II):

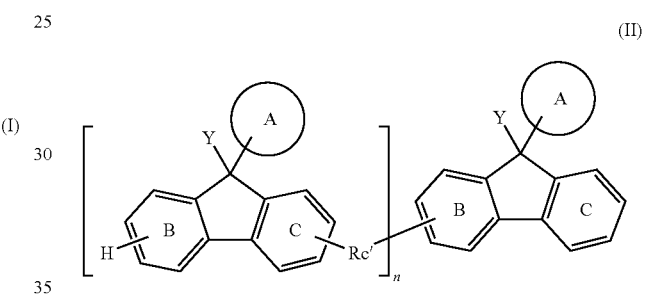

(II)

wherein ring A is an aromatic ring; Y is a group reactive with one or more kinds selected from an amino group, a carboxyl group and a mercapto group; n is an integer of 1 to 19; Rc' is a divalent organic group having an aliphatic hydrocarbon group; rings A, B and C each independently optionally have one or more kinds selected from an organic group having an aliphatic hydrocarbon group and an electron-withdrawing group; when a plurality of ring A is present, respective rings A may be the same or different; when a plurality of Y is present, respective Y may be the same or different; and when a plurality of Rc' is present, respective Rc' may be the same or different.

(5) The fluorene compound of any one of the above-mentioned (1)-(4), wherein the organic group having an aliphatic hydrocarbon group and/or the divalent organic group having an aliphatic hydrocarbon group is bonded on the ring via —O—, —S—, —NHCO— or —CONH— present in the organic group, or directly bonded to form a carbon-carbon bond.

(6) The fluorene compound of any one of the above-mentioned (1)-(5), wherein the organic group having an aliphatic hydrocarbon group and/or the divalent organic group having an aliphatic hydrocarbon group has a structure comprising 2 to 10 connections of an aliphatic hydrocarbon group bonded via —O—, —S—, —NHCO— or —CONH—, or an aliphatic hydrocarbon group directly bonded to form a carbon-carbon bond.

(7) The fluorene compound of the above-mentioned (4), wherein the divalent organic group having an aliphatic hydrocarbon group for Rc' is a group represented by formula (i):

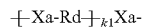

(i)

wherein Xa is absent or —O—, —S—, —NHCO— or —CONH—; Rd is an aliphatic hydrocarbon group having a carbon number of not less than 5; $k_1$ is an integer of 1-10; when a plurality of Rd is present, respective Rd may be the same or different; and when a plurality of Xa is present, respective Xa may be the same or different.

(8) The fluorene compound of the above-mentioned (4), wherein the divalent organic group having an aliphatic to hydrocarbon group for Rc' is a group represented by formula (ii):

wherein Re is an aliphatic hydrocarbon group having a carbon number of 5 to 60; $k_2$ is an integer of 1 to 3; and when a plurality of Re is present, respective Re may be the same or different.

(9) The fluorene compound of any one of the above-mentioned (1)-(8), wherein the organic group having an aliphatic hydrocarbon group is one or more kinds of group selected from a group represented by formula (a):

wherein * shows the position of a bond; $X_1$ is absent or —O—, —S—, —NHCO— or —CONH—; $R_1$ is an aliphatic hydrocarbon group having a carbon number of not less than 5; $m_1$ is an integer of 1 to 10; when a plurality of $X_1$ is present, respective $X_1$ may be the same or different; and when a plurality of $R_1$ is present, respective $R_1$ may be the same or different;

a group represented by the formula (b):

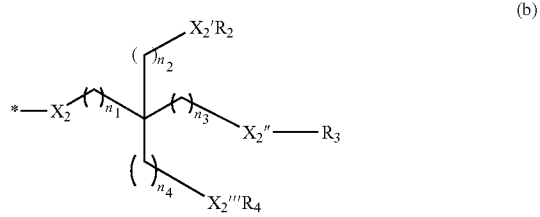

wherein * shows the position of a bond; $X_2$, $X_2'$, $X_2''$ and $X_2'''$ are each independently absent or —O—, —S—, —NHCO— or —CONH—; $R_2$ and $R_4$ are each independently a hydrogen atom, an aliphatic hydrocarbon group having a carbon number of not less than 5 or a methyl group, $R_3$ is an organic group having an aliphatic hydrocarbon group having a carbon number of not less than 5; $n_1$, $n_2$, $n_3$ and $n_4$ are each independently an integer of 0 to 2; $m_2$ is an integer of 1 or 2; when a plurality of $n_1$, $n_2$, $n_3$ and $n_4$ are each present, each respective $n_1$, $n_2$, $n_3$ and $n_4$ may be the same or different; when a plurality of $X_2'$, $X_2''$ and $X_2'''$ are each present, each respective $X_2'$, $X_2''$ and $X_2'''$ may be the same or different; and when a plurality of $R_2$ and $R_4$ are each present, each respective $R_2$ and $R_4$ may be the same or different; and a group represented by the formula (e):

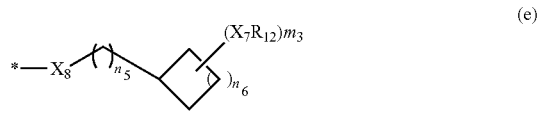

wherein * shows the position of a bond; $X_8$ is absent or —O—, —S—, —NHCO— or —CONH—; $m_3$ is an integer of 0 to 15; $n_5$ is an integer of 0 to 11; $n_6$ is an integer of 0 to 5; $X_7$ is absent or —O—, —S—, —COO—, —OCONH—, —NHCO— or —CONH—; $R_{12}$ is a hydrogen atom, a methyl group or an aliphatic hydrocarbon group having a carbon number of not less than 5; when a plurality of $X_7$ is present, respective $X_7$ may be the same or different; and when a plurality of $R_{12}$ is present, respective $R_{12}$ may be the same or different.

(10) The fluorene compound of the above-mentioned (9), wherein, in the formula (a), $X_1$ is —O—; $R_1$ is an aliphatic hydrocarbon group having a carbon number of 5 to 60; $m_1$ is 1;

in the formula (b), $X_2$ is —O—, or —CONH—; $X_2'$, $X_2''$ and $X_2'''$ are each independently absent, or —O—; $R_2$ and $R_4$ are each independently an aliphatic hydrocarbon group having a carbon number of 5 to 60 or a methyl group; $R_3$ is an organic group having an aliphatic hydrocarbon group having a carbon number 5 to 60; $n_1$, $n_2$, $n_3$ and $n_4$ are the same or different and each is an integer of 0 or 1; $m_2$ is 1, and in the formula (e), $X_8$ is —O—; $m_3$ is 2 or 3; $n_5$ is 1; $n_6$ is 2 or 3; $X_7$ is —O—; and $R_{12}$ in the number of $m_3$ are each independently an alkyl group having a carbon number of 8 to 60.

(11) The fluorene compound of any one of the above-mentioned (1)-(6), wherein the aliphatic hydrocarbon group of the organic group having an aliphatic hydrocarbon group and/or the divalent organic group having an aliphatic hydrocarbon group is an aliphatic hydrocarbon group having a carbon number of not less than 5.

(12) The fluorene compound of any one of the above-mentioned (1)-(6), wherein the aliphatic hydrocarbon group of the organic group having an aliphatic hydrocarbon group and/or the divalent organic group having an aliphatic hydrocarbon group is an aliphatic hydrocarbon group having a carbon number of 5 to 60.

(13) The fluorene compound of any one of the above-mentioned (1)-(12), wherein the total carbon number derived from an aliphatic hydrocarbon group in one molecule is not less than 20.

(14) The fluorene compound of any one of the above-mentioned (1)-(12), wherein the total carbon number derived from an aliphatic hydrocarbon group in one molecule is 20 to 200.

(15) The fluorene compound of any one of the above-mentioned (1)-(14), wherein Y is a hydroxyl group, a bromo group, a chloro group, an iodo group, a thiol group or an amino group.

(16) The fluorene compound of any one of the above-mentioned (1)-(14), wherein Y is a hydroxyl group, a bromo group or a chloro group.

(17) The fluorene compound of any one of the above-mentioned (1)-(16), wherein the aromatic ring of ring A is a benzene ring.

(18) The fluorene compound of the above-mentioned (3), wherein Ra is a halogen atom.

(19) The fluorene compound of the above-mentioned (3), wherein the organic group having an aliphatic hydrocarbon group is present at the 2-position and/or the 7-position of the fluorene compound.

(20) The fluorene compound of the above-mentioned (3), wherein Rb and/or Rc are/is a group represented by the formula (a) wherein $m_1$ is 1; $X_1$ is —O—; and $R_1$ is an aliphatic hydrocarbon group having a carbon number of 5 to 60, a group represented by the formula (b) wherein $X_2$, $X_2'$, $X_2''$ and $X_2'''$ are each —O—; $R_2$ and $R_4$ are each independently an aliphatic hydrocarbon group having a carbon number of 5 to 60; $R_3$ is an organic group having an aliphatic hydrocarbon group having a carbon number of 5 to 60; $n_1$, $n_2$, $n_3$ and $n_4$ are each 1; and $m_2$ is 1, or a group represented by the formula (e) wherein $X_8$ is —O—; $m_3$ is 2 or 3; $n_5$ is 1; $n_6$ is 3; $X_7$ is —O—; and $R_{12}$ in the number of $m_3$ are each independently an alkyl group having a carbon number of 14 to 30.

(21) The fluorene compound of the above-mentioned (3), wherein ring A is a benzene ring; Y is a hydroxyl group, a bromo group or a chloro group; Ra is a halogen atom; and an organic group having an aliphatic hydrocarbon group is a group represented by the formula (a) wherein $m_1$ is 1; $X_1$ is —O—; and $R_1$ is an aliphatic hydrocarbon group having a carbon number of 5 to 60, a group represented by the formula (b) wherein $X_2$, $X_2'$, $X_2''$ and $X_2'''$ are each —O—; $R_2$ and $R_4$ are each independently an aliphatic hydrocarbon group having a carbon number of 5 to 60; $R_3$ is an organic group having an aliphatic hydrocarbon group having a carbon number 5 to 60; $n_1$, $n_2$, $n_3$ and $n_4$ are each 1; and $m_2$ is 1, or a group represented by the formula (e) wherein $X_8$ is —O—; $m_3$ is 2 or 3; $n_5$ is 1; $n_6$ is 3; $X_7$ is —O—; and $R_{12}$ in the number of $m_3$ are each independently an alkyl group having a carbon number of 14 to 30, each of which formulas is present at the 2-position and/or the 7-position of the fluorene compound.

(22) The fluorene compound of the above-mentioned (4), wherein n is 1.

(23) The fluorene compound of the above-mentioned (4), wherein ring A has an electron-withdrawing group.

(24) The fluorene compound of the above-mentioned (23), wherein the electron-withdrawing group is a halogen atom.

(25) The fluorene compound of the above-mentioned (4), wherein Rc' is a group represented by the formula (i) wherein Xa is —O—; Rd in the number of $k_1$ are each independently an aliphatic hydrocarbon group having a carbon number of 5 to 60, and $k_1$ is an integer of 1 to 3.

(26) The fluorene compound of the above-mentioned (4), wherein ring A is a benzene ring; Y is a hydroxyl group, a bromo group or a chloro group; n is 1; ring A has a halogen atom as the electron-withdrawing group; Rc' is a group represented by the formula (i) wherein Xa is —O—; Rd is an aliphatic hydrocarbon group having a carbon number of 5 to 60, and $k_1$ is an integer of 1 to 3.

(27) The fluorene compound of the above-mentioned (3) or (4), which is selected from the group consisting of
2-docosyloxy-9-(4-chlorophenyl)-9-fluorenol;
2-docosyloxy-9-(4-chlorophenyl)-9-bromofluorene;
2,7-didocosyloxy-9-(4-chlorophenyl)-9-bromofluorene;
2-(12-docosyloxy-dodecanoxy)-9-(3-fluorophenyl)-9-bromofluorene;
1,12-bis-[12-(2'-O-9-(4-chlorophenyl)-9-fluorenol)-dodecyloxy]-dodecane;
1,12-bis-[12-(2'-O-9-(4-chlorophenyl)-9-bromofluorene)-dodecyloxy]-dodecane;
2-(3-octadecyloxy-2,2-bis-octadecyloxymethyl-propoxy)-9-(4-chlorophenyl)-9-fluorenol;
2-(3-octadecyloxy-2,2-bis-octadecyloxymethyl-propoxy)-9-(4-chlorophenyl)-9-bromofluorene;
9-(4-chlorophenyl)-2-(3,4,5-tris(octadecyloxy)-cyclohexylmethoxy)-9-fluorenol; and
9-(4-chlorophenyl)-2-(3,4,5-tris(octadecyloxy)-cyclohexylmethoxy)-9-bromofluorene.

(28) A protecting reagent for organic synthesis reaction, comprising the fluorene compound of any one of the above-mentioned (1)-(27).

(29) A protecting reagent for a carboxyl group of amino acid or peptide, comprising the fluorene compound of any one of the above-mentioned (1)-(27).

(30) A protecting reagent for the C-terminal of amino acid or peptide, comprising the fluorene compound of any one of the above-mentioned (1)-(27).

(31) A method of producing a peptide by a liquid phase synthesis process comprising the following steps;

(a) a step of binding a fluorene compound of any one of the above-mentioned (1)-(27) to an amino acid or peptide (binding step), and (b) a step of precipitating the bonded product of the compound and the amino acid or peptide obtained in the above-mentioned step (precipitation step).

(32) A method of producing a peptide by a liquid phase synthesis process comprising the following steps;

(a) a step of obtaining C-fluorene compound-protected amino acid or C-fluorene compound-protected peptide by condensing a fluorene compound of any one of the above-mentioned (1)-(27) with the C-terminal of an N-protected amino acid or N-protected peptide (C-terminal fluorene compound protection step), (b) a step of removing the protecting group of the N-terminal of the amino acid or peptide obtained in the above-mentioned step (N-terminal deprotection step), (c) a step of condensing the N-terminal of the amino acid or peptide obtained in the above-mentioned step with N-protected amino acid or N-protected peptide (peptide chain elongation step), and (d) a step of precipitating the peptide obtained in the above-mentioned step (precipitation step).

(33) The method of the above-mentioned (32), further comprising one or more repeats of the following steps (e)-(g):

(e) a step of deprotecting the N-terminal of the peptide obtained in the precipitation step, (f) a step of condensing the N-terminal of peptide obtained in the above-mentioned step with N-protected amino acid or N-protected peptide, and (g) a step of precipitating the peptide obtained in the above-mentioned step.

(34) A method of producing a peptide further comprising, after the final precipitation step of the above-mentioned (32) or (33), a step of deprotecting the C-terminal of peptide wherein the C-terminal is protected with a fluorene compound.

(35) A method of producing a peptide compound, comprising using a fluorene compound of any one of the above-mentioned (1)-(27).

(36) A method of producing an organic compound, 35 comprising using a fluorene compound of any one of the above-mentioned (1)-(27).

(37) A compound represented by the following formula (III):

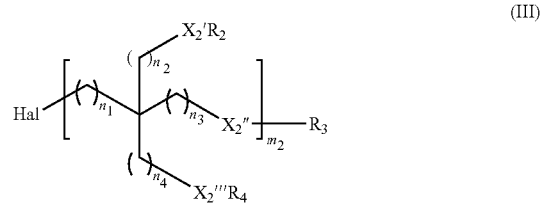

wherein $X_2'$, $X_2''$ and $X_2'''$ are each independently absent or —O—, —S—, —NHCO— or —CONH—; $R_2$ and $R_4$ are each independently a hydrogen atom, an aliphatic hydrocarbon group having a carbon number of not less than 5 or a methyl group; $R_3$ is an organic group having an aliphatic hydrocarbon group having a carbon number of not less than 5; $n_1$, $n_2$, $n_3$ and $n_4$ are each independently an integer of 0 to 2; $m_2$ is an integer of 1 or 2; when a plurality of $n_1$, $n_2$, $n_3$ and $n_4$ are each present, each respective $n_1$, $n_2$, $n_3$ and $n_4$ may be the same or different; when a plurality of $X_2'$, $X_2''$ and $X_2'''$ are each present, each respective $X_2'$, $X_2''$ and $X_2'''$ may be the same or different; and a plurality of when $R_2$ and $R_4$ are each present, each respective $R_2$ and $R_4$ may be the same or different; and Hal is a halogen atom.

(38) The compound of the above-mentioned (37), wherein, in the formula (III), $X_2'$, $X_2''$ and $X_2'''$ are the same or different and each is absent or —O—; $R_2$ and $R_4$ are each independently an aliphatic hydrocarbon group having a carbon number of 10 to 30 or a methyl group; $R_3$ is an organic group having an aliphatic hydrocarbon group having a carbon number of 10 to 30; $n_1$, $n_2$, $n_3$ and $n_4$ are the same or different and each is an integer of 0 or 1; and $m_2$ is 1.

(39) The compound of the above-mentioned (37), which is 1-(3-iodo-2,2-bis-octadecanoxymethyl-propoxy)octadecane.

The compounds of the present invention are superior in broad utility and stability in organic synthesis reactions, particularly peptide synthesis reactions. When peptide synthesis is performed using a compound of the present invention as an anchor, a sequence that easily forms diketopiperazine can be synthesized in a high yield, and further, the anchor can be selectively removed. Thus, a protected peptide can be directly obtained without removing other protecting groups (peptide-side chain protecting group etc.).

The particular compounds of the present invention having a fluorene skeleton function as a superior protecting group and anchor, and the anchor can be removed under weak acidic conditions, and selectively removed even when other protecting groups (peptide side chain protecting group etc.) still remain in the compound obtained by organic synthesis reactions. Namely, the compound is a substance that enables easy precipitation in methanol and the like, since it dissolves only in halogen solvents, THF and the like and scarcely dissolves in polar organic solvents. In the process of elongation of peptide chain length wherein the substance is used as a protecting group for C-terminal or side chain in the peptide synthesis and an operation including reaction in a halogen solvent, followed by precipitation with methanol and the like to remove impurity is repeated, a side reaction giving diketopiperazine is suppressed and the peptide chain can be elongated in a high yield and with high quality. Moreover, the anchor enables selective removal thereof while maintaining the protecting group.

DETAILED DESCRIPTION OF THE PREFERRED EMBODIMENTS

Unless otherwise specified in the sentences, any technique terms and scientific terms used in the present specification, have the same meaning as those generally understood by those of ordinary skill in the art in the art the present invention belongs to. Any methods and materials similar or equivalent to those described in the present specification can be used for practicing or testing the present invention, and preferable methods and materials are described in the following. All publications and patents referred to in the Specification are hereby incorporated by reference so as to describe and disclose constructed products and methodology described in, for example, publications usable in relation to the described invention.

1. The Compounds of the Present Invention

The compound of the present invention is useful as a reagent for organic synthesis. Here, the reagent for organic synthesis refers to any reagent relating to organic synthesis reactions, and is a concept including reagents directly involved in the reaction such as reaction substrate, reaction promoter, reagent for introducing protecting group, deprotecting agent and the like, as well as inert solvent and the like. Specifically, reagents to be used for peptide synthesis reaction are exemplified. Preferred is a reagent introduced as a protecting group (anchor) of the C-terminal of amino acid or peptide in liquid phase synthesis of peptide, and a reagent introduced as a protecting group as a peptideside chain protecting group in peptide synthesis reaction, and an appropriate compound can be selected according to the object. Particularly preferable compounds of the present invention are anchors.

One embodiment of the compound of the present invention is a fluorene compound represented by the following formula (I):

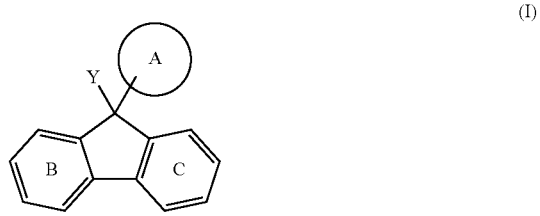

wherein ring A is an aromatic ring; Y is a group reactive with one or more kinds selected from an amino group, a carboxyl group and a mercapto group; at least one of rings A, B and C has an organic group having an aliphatic hydrocarbon group; and rings A, B and C each independently optionally have an electron-withdrawing group.

A fluorene compound represented by the following formula (I'), wherein at least one of rings A, B and C has "an organic group having an aliphatic hydrocarbon group" and the number of "an organic group having an aliphatic hydrocarbon group" of each ring is 1 to 4, preferably 1 to 3, more preferably 1 or 2, still more preferably 1 or 0, is more preferable.

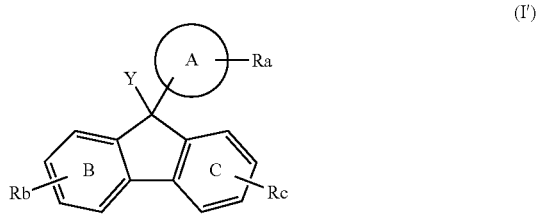

wherein ring A is an aromatic ring; Y is a group reactive with one or more kinds selected from an amino group, a carboxyl group and a mercapto group; Ra, Rb and Rc are each independently an organic group having an aliphatic hydrocarbon group, a hydrogen atom or an electron-withdrawing group, and at least one of Ra, Rb and Rc is an organic group having an aliphatic hydrocarbon group; and rings A, B and C each independently optionally have an electron-withdrawing group.

A fluorene compound represented by the formula (I') is encompassed in a fluorene compound represented by the formula (I).

Moreover, the compound of the present invention may be a compound having a structure as shown below, wherein a plurality of divalent unit structures derived from a compound represented by the formula (I) are connected. Preferred is a fluorene compound wherein 2 to 20 of a divalent unit structure derived from a compound represented by the following formula (I):

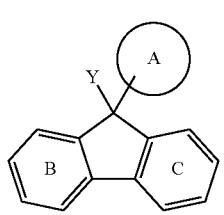

(I)

wherein ring A is an aromatic ring; Y is a group reactive with one or more kinds selected from an amino group, a carboxyl group and a mercapto group; at least one of rings A, B and C has an organic group having an aliphatic hydrocarbon group; and rings A, B and C each independently optionally have an electron-withdrawing group,
are connected via an organic group having an aliphatic hydrocarbon group, which the unit structure has.

As the above-mentioned compound, a compound represented by the following formula (II) is also preferable.

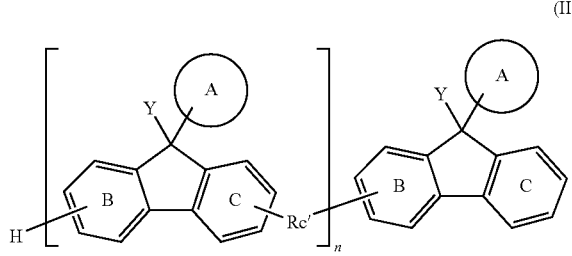

(II)

wherein ring A is an aromatic ring; Y is a group reactive with one or more kinds selected from an amino group, a carboxyl group and a mercapto group; n is an integer of 1 to 19; Rc' is a divalent organic group having an aliphatic hydrocarbon group; rings A, B and C each independently optionally have one or more kinds selected from an organic group having an aliphatic hydrocarbon group and an electron-withdrawing group; when a plurality of ring A is present, respective rings A may be the same or different; when a plurality of Y is present, respective Y may be the same or different; and when plurality of Rc' is present, respective Rc' may be the same or different.

The divalent organic group having an aliphatic hydrocarbon group for Rc' is preferably represented by the following formula (i).

(i)

wherein Xa is absent or —O—, —S—, —NHCO—, or —CONH—; Rd is an aliphatic hydrocarbon group having a carbon number of not less than 5; $k_1$ is an integer of 1 to 10; when a plurality of Rd is present, respective Rd may be the same or different; and when a plurality of Xa is present, respective Xa may be the same or different.

In formula (i), Xa is preferably —O—, Rd is preferably an aliphatic hydrocarbon group having a carbon number of 5 to 60, and $k_1$ is preferably an integer of 1 to 3. That is, preferably formula (i) is represented by the following formula (ii).

(ii)

wherein Re is an aliphatic hydrocarbon group having a carbon number of 5 to 60; $k_2$ is an integer of 1 to 3; and when a plurality of Re is present, respective Re may be the same or different.

In the present specification, the "aromatic ring" means an "aromatic hydrocarbon ring" or an "aromatic heterocycle".

As the "aromatic hydrocarbon ring", $C_{6-14}$ arene (e.g., benzene, naphthalene and the like) is preferable, $C_{6-10}$ arene is more preferable, and benzene is particularly preferable.

Examples of the "aromatic heterocycle" include a 5- to 7-membered monocyclic aromatic heterocycle or condensed aromatic heterocycle containing, as a ring-constituting atom besides carbon atom, 1 to 4 hetero atoms selected from an oxygen atom, a sulfur atom and a nitrogen atom. Examples of the condensed aromatic heterocycle include a group wherein such 5- to 7-membered monocyclic aromatic heterocycle and a 6-membered ring containing 1 or 2 nitrogen atoms, benzene ring, or a 5-membered ring containing one sulfur atom are condensed and the like.

Preferable examples of the "aromatic heterocycle" include 5 to 7-membered monocyclic aromatic heterocycle such as furan, thiophene, pyrrole, oxazole, isoxazole, thiazole, isothiazole, imidazole, pyrazole, 1,2,3-oxadiazole, 1,2,4-oxadiazole, 1,3,4-oxadiazole, furazan, 1,2,3-thiadiazole, 1,2,4-thiadiazole, 1,3,4-thiadiazole, 1,2,3-triazole, 1,2,4-triazole, tetrazole, pyridine, pyridazine, pyrimidine, pyrazine, triazine and the like; 8- to 16-membered (preferably 8- to 12-membered) condensed aromatic heterocycle (preferably heterocycle wherein one or two (preferably one) 5- to 7-membered monocyclic aromatic heterocycle mentioned above is condensed with one or two (preferably one) benzene rings, or heterocycle wherein the same or different two or three (preferably two) 5- to 7-membered monocyclic aromatic heterocycles mentioned above are condensed) such as benzofuran, isobenzofuran, benzo[b]thiophene, benzo[c]thiophene, indole, isoindole, 1H-indazole, benzimidazole, benzoxazole, 1,2-benzisoxazole, benzothiazole, 1,2-benzisothiazole, 1H-benzotriazole, quinoline, isoquinoline, cinnoline, quinazoline, quinoxaline, phthalazine, naphthyridine, purine, pteridinee, carbazole, α-carboline, β-carboline, γ-carboline, acridine, phenoxathiine, phenothiazine, phenazine, phenoxathiine, thianthrene, phenanthridine, phenanthrolin, indolizine, pyrrolopyridine, pyrrolo[1,2-b]pyridazine, pyrazolo[1,5-a]pyridine, imidazo[1,2-a]pyridine, imidazo[1,5-a]pyridine, imidazo[1,2-b]pyridazine, imidazo[1,2-a]pyrimidine, 1,2,4-triazolo[4,3-a]pyridine, 1,2,4-triazolo[4,3-b]pyridazine, and the like, and the like.

When desired, the "aromatic ring" optionally further has substituent(s) besides the organic group having an aliphatic hydrocarbon group in the formula (I) and the Ra group in the formula (I'). Examples of the further substituent include an electron-withdrawing group and the like. Specific examples of the further substituent include a halogen atom (chlorine atom, bromine atom, fluorine atom, iodine atom), optionally halogenated alkyl group (trifluoromethyl group etc.), nitro group, cyano group, ester group [alkoxycarbonyl group (methoxycarbonyl group, ethoxycarbonyl group, propoxycarbonyl group etc.), aryloxycarbonyl group (phenyloxycarbonyl group etc.)] and the like.

In the present specification, examples of the "group reactive with an amino group, a carboxyl group and/or a mercapto group" include a hydroxyl group, a bromo group, a chloro group, an iodo group, a thiol group, an amino group and the like, with preference given to a hydroxyl group, a bromo group and a chloro group.

The amino group, carboxyl group and/or mercapto group are present in an amino acid or peptide, which is a starting material of the peptide synthesis. That is, the compound represented by the formula (I), the formula (I') or the formula (II) of the present invention is bonded to amino acid or peptide via Y group which is a "group reactive with an amino group, a carboxyl group and/or a mercapto group". Preferably, in the liquid phase synthesis of peptide, it can function as an anchor of the C-terminal (C-terminal protecting reagent) of an amino acid or peptide to be the starting material, and/or as a side chain-protecting group (e.g., a carboxyl-protecting reagent).

Here, the "side chain" is a chained structure other than the main chain present in an amino acid or peptide to be the starting material. For example, an acidic amino acid such as aspartic acid and glutamic acid also has a carboxyl group in the side chain, an amino group in lysine and mercapto group in cysteine.

In the present specification, the "electron-withdrawing group" includes those generally used in the art. Specifically, a halogen atom (chlorine atom, bromine atom, fluorine atom, iodine atom), a nitro group, a perhalogenoalkyl group (e.g., trifluoromethyl group), a cyano group, a carboxyl group, an alkoxycarbonyl group (e.g., methoxycarbonyl group, ethoxycarbonyl group), an aryloxycarbonyl group (e.g., phenyloxycarbonyl group), an alkylamide group (e.g., acetamide group), a perhalogenoalkylamide group (e.g., trifluoroacetamido group), an optionally substituted alkanoyl group (e.g., acetyl group, ethanoyl group, propanoyl group, isopropanoyl group, butanoyl group, isobutanoyl group, trifluoroacetyl group), an optionally substituted aroyl group (e.g., benzoyl group, naphthylcarbonyl group, p-chlorobenzoyl group), an optionally substituted alkylsulfonyl group (e.g., methanesulfonyl group, trifluoromethanesulfonyl group), an optionally substituted arylsulfonyl group (e.g., benzenesulfonyl group, p-toluenesulfonyl group), an optionally substituted alkylsulfoneamide group (e.g., methanesulfoneamide group, trifluoromethanesulfoneamide group), an optionally substituted arylsulfonamide group (e.g., benzenesulfoneamide group or p-toluenesulfoneamide group) and the like can be mentioned. Preferred are fluorine atom, chlorine atom, nitro group, trifluoromethyl group, cyano group, trifluoroacetamido group, trifluoroacetyl group, p-chlorobenzoyl group, methanesulfonyl group, trifluoromethanesulfonyl group, benzenesulfonyl group, p-toluenesulfonyl group, methanesulfoneamide group, trifluoromethanesulfoneamide group, benzenesulfoneamide group, p-toluenesulfoneamide and the like, and particularly preferred are halogen atom and trifluoromethyl group.

In the present specification, the "organic group having an aliphatic hydrocarbon group" means a monovalent organic group (one bond is bonded to at least one of rings A, B and C) which has an aliphatic hydrocarbon group in the molecular structure.

The "aliphatic hydrocarbon group" of the "organic group having an aliphatic hydrocarbon group" is a aliphatic hydrocarbon group consisting of straight chain or branched, saturated or unsaturated carbon and hydrogen, and an aliphatic hydrocarbon group having a carbon number of not less than 5 is preferable, an aliphatic hydrocarbon group having a carbon number of 5 to 60 is particularly preferable, an aliphatic hydrocarbon group having a carbon number of 5 to 30 is more preferable, and an aliphatic hydrocarbon group having a carbon number of 10 to 30 is further preferable.

The site of the "aliphatic hydrocarbon group" in the organic group having an aliphatic hydrocarbon group of is not particularly limited, and it may be present at the terminal (monovalent group), or other site (for example, divalent group).

Specific examples of the aliphatic hydrocarbon group include monovalent groups such as methyl group, ethyl group, propyl group, isopropyl group, butyl group, isobutyl group, sec-butyl group, tert-butyl group, pentyl group, hexyl group, octyl group, decyl group, lauryl group, tridecyl group, myristyl group, cetyl group, stearyl group, aralkyl group, behenyl group, oleyl group, isostearyl group and the like and a divalent group derived therefrom.

In the "organic group having an aliphatic hydrocarbon group", a moiety other than the aliphatic hydrocarbon group can be set freely. For example, it optionally has a moiety such as —O—, —S—, —NHCO—, —CONH—, hydrocarbon group and the like. Examples of the "hydrocarbon group" include a monovalent group such as aliphatic hydrocarbon group, monocyclic saturated hydrocarbon group and aromatic hydrocarbon group and the like, specific examples include alkyl group, alkenyl group, alkynyl group, cycloalkyl group, aryl group and the like and a divalent group derived therefrom. Examples of the "alkyl group" include $C_{1-6}$ alkyl group and the like and preferable examples include methyl, ethyl, propyl, isopropyl, butyl, isobutyl, sec-butyl, tert-butyl, pentyl, hexyl and the like. Examples of the "alkenyl group" include $C_{2-6}$ alkenyl group and the like and preferable examples include vinyl, 1-propenyl, allyl, isopropenyl, butenyl, isobutenyl and the like. Examples of "alkynyl group" include $C_{2-6}$ alkynyl group and the like and preferable examples include ethynyl, propargyl, 1-propynyl and the like. Examples of the "cycloalkyl group" include $C_{3-6}$ cycloalkyl group and the like and preferable examples include cyclopropyl, cyclobutyl, cyclopentyl and cyclohexyl. The "aryl group" is preferably, for example, $C_{6-14}$ aryl group such as phenyl, 1-naphthyl, 2-naphthyl, biphenylyl, 2-anthryl and the like, and the like, more preferably $C_{6-10}$ aryl group and, for example, phenyl group and the like. The hydrocarbon group is optionally substituted by a substituent selected from a halogen atom (chlorine atom, bromine atom, fluorine atom, iodine atom), an oxo group and the like.

The "organic group having an aliphatic hydrocarbon group" may be bonded (substitution) to at least one of rings A, B and C via an aliphatic hydrocarbon group present in the group, namely, directly bonded to form a carbon-carbon bond or via —O—, —S—, —NHCO—, —CONH— and the like present in the group. Preferably, it is bonded via —O—, —S— or —CONH— in view of the easiness of synthesis of the compound. More preferably, it is bonded via —O—.

The compound of in the present invention is characterized in that ring A, B and/or C are/is substituted by 1 to 4, preferably 1 to 3, more preferably 1 or 2, "organic groups having an aliphatic hydrocarbon group" mentioned above. A same ring may be substituted by all "organic groups having an aliphatic hydrocarbon group", a different ring may be substituted thereby. In addition, plural aliphatic hydrocarbon groups may be contained in one "organic group having an aliphatic hydrocarbon group" by branching and the like. In the compound of the present invention, when a plurality of aliphatic hydrocarbon group is present, they may be the same or different.

In the compound of the present invention, an organic group having an aliphatic hydrocarbon group is unlimitatively preferably bonded to the 2-position and/or the 7-position on the fluorene ring in the compound of the present invention, since the final deanchoring is easy.

The "aliphatic hydrocarbon group" in the compound of the present invention is appropriately selected according to the use of the compound to be synthesized. For example, when it is use as a peptideside chain-protecting group in the peptide synthesis, one having a comparatively short chain length, for example, one having a carbon number of less than 5 can be employed. When it is used as an anchor at the C-terminal of an amino acid or peptide, one having a comparatively long chain length, namely, one having a carbon number of not less than 5 is preferably employed. Furthermore, an aliphatic hydrocarbon group having a carbon number of 5 to 60 is more preferable, an aliphatic hydrocarbon group having a carbon number of 5 to 30 is further preferable, and an aliphatic hydrocarbon group having a carbon number of 10 to 30 is still more preferable. When it is used as an anchor, the total number of carbon derived from the "aliphatic hydrocarbon group" in one molecule of the compound of the present invention (hereinafter to be also referred to as the total carbon number derived from aliphatic hydrocarbon group; when a plurality of "aliphatic hydrocarbon group" is present, the total thereof) is preferably not less than 20, more preferably 20 to 200, further preferably 20 to 100, and still more preferably 20 to 60. When the carbon number is higher, crystallinity of the compound of the present invention in a polar organic solvent becomes fine even when the peptide chain is a long chain.

Examples of the "organic group having an aliphatic hydrocarbon group" include the groups represented by the following formulas (a) to (e).

In the formula (a), * shows the position of a bond; $X_1$ is absent or —O—, —S—, —NHCO— or —CONH—; $R_1$ is an aliphatic hydrocarbon group having a carbon number of not less than 5; $m_1$ is an integer of 1 to 10; when a plurality of $X_1$ is present, respective $X_1$ may be the same or different; and when a plurality of $R_1$ is present, respective $R_1$ may be the same or different.

In the formula (a), particularly a group wherein $X_1$ is —O—; $R_1$ is an aliphatic hydrocarbon group having a carbon number of 5 to 60; and $m_1$ is 1, is preferable.

As the "aliphatic hydrocarbon group having a carbon number of not less than 5" for $R_1$, an "aliphatic hydrocarbon group" of the above-mentioned "organic group having an aliphatic hydrocarbon group", which has a carbon number of not less than 5 can be mentioned, with preference given to on having a carbon number of 5 to 60.

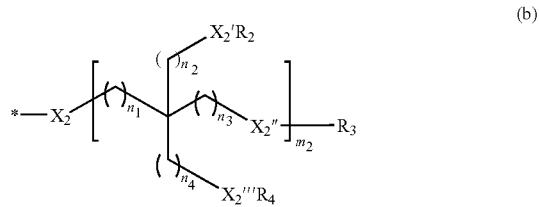

In the formula (b), shows the position of a bond; $X_2$, $X_2'$, $X_2''$ and $X_2'''$ are each independently absent, or —O—, —S—, —NHCO— or —CONH—; $R_2$ and $R_4$ are each independently a hydrogen atom, an aliphatic hydrocarbon group having a carbon number of not less than 5 or a methyl group; $R_3$ is an organic group having an aliphatic hydrocarbon group having a carbon number of not less than 5; $n_1$, $n_2$, $n_3$ and $n_4$ are each independently an integer of 0 to 2; $m_2$ is an integer of 1 or 2; when a plurality of $n_1$, $n_2$, $n_3$ and $n_4$ are present, each respective $n_1$, $n_2$, $n_3$ and $n_4$ may be the same or different; when a plurality of $X_2'$, $X_2''$ and $X_2'''$ are present, each respective $X_2'$, $X_2''$ and $X_2'''$ may be the same or different; and when a plurality of $R_2$ and $R_4$ are present, each respective $R_2$ and $R_4$ may be the same or different.

As the "aliphatic hydrocarbon group having a carbon number of not less than 5" for $R_2$, $R_3$ or $R_4$, from among the above-mentioned "organic group having an aliphatic hydrocarbon group", an "aliphatic hydrocarbon group" having a carbon number of not less than 5 can be mentioned, with preference given to one having a carbon number of 5 to 60.

In the formula (b), a group wherein $X_2$ is —O—, —NHCO— or —CONH—, preferably —O— or —CONH—; $X_2'$, $X_2''$ and $X_2'''$ are each independently absent or —O—; $R_2$ and $R_4$ are each independently an aliphatic hydrocarbon group having a carbon number of 5 to 60 or a methyl group; $R_3$ is an organic group having an aliphatic hydrocarbon group having a carbon number 5 to 60; $n_1$, $n_2$, $n_3$ and $n_4$ are the same or different and each is an integer of 0 or 1; and $m_2$ is 1, is particularly preferable.

In the formula (b), a group wherein $X_2$, $X_2'$, $X_2''$ and $X_2'''$ are each —O—, $R_2$ and $R_4$ are each independently an aliphatic hydrocarbon group having a carbon number of 5 to 60, $R_3$ is an organic group having an aliphatic hydrocarbon group having a carbon number 5 to 60, $n_1$, $n_2$, $n_3$ and $n_4$ are each 1, and $m_2$ is 1, is more preferable.

In the formula (c), shows the position of a bond; $X_3$ and $X_3'$ are the same or different and each is absent or —O—, —S—, —NHCO— or —CONH—; $R_5$ and $R_6$ are the same or different and each is an aliphatic hydrocarbon group; and Ar is an arylene group.

Examples of the "arylene group" include phenylene, naphthylene, biphenylene and the like, with preference given to phenylene.

As the "aliphatic hydrocarbon group" for $R_5$ or $R_6$, those similar to the "aliphatic hydrocarbon group" of the above-mentioned "organic group having an aliphatic hydrocarbon group" can be mentioned, particularly one having a carbon number of not less than 5 preferably 5 to 60, can be mentioned.

In the formula (c), a group wherein $X_3$ and $X_3'$ are each —O—; $R_5$ and $R_6$ are each independently an aliphatic hydrocarbon group having a carbon number of 5 to 60; and Ar is phenylene, is particularly preferable.

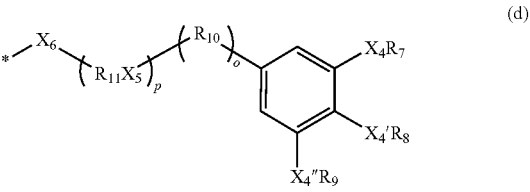

In the formula (d), * shows the position of a bond; o and p are each 0 or 1; $X_4$, $X_4'$, $X_4''$, $X_5$ and $X_6$ are the same or different and each is absent, or —O—, —S—, —NHCO— or —CONH—; $R_7$, $R_8$ and $R_9$ are the same or different and each is an aliphatic hydrocarbon group and $R_{10}$ and $R_{11}$ are each an alkylene group having a carbon number of 1 to 10.

Examples of the "alkylene group" having a carbon number of 1 to 10 include methylene, ethylene, propylene, butylene, hexylene, octylene, dodecylene and the like.

As the "aliphatic hydrocarbon group" for $R_7$-$R_9$, those similar to the "aliphatic hydrocarbon group" of the above-mentioned "organic group having an aliphatic hydrocarbon group" can be mentioned, particularly one having a carbon number of not less than 5 can be mentioned, preferably one having a carbon number of 5 to 60.

In the formula (d), a group wherein o is 0; p is 1; $X_4$, $X_4'$ and $X_4''$ are each —O—; $X_5$ is —NHCO—; $X_6$ is —O—; $R_7$-$R_9$ is an aliphatic hydrocarbon group having a carbon number of 5 to 60; $R_{10}$ and $R_{11}$ are each an alkylene group having a carbon number of 1 to 10, is particularly preferable.

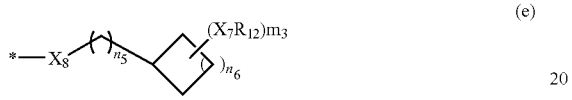

(e)

wherein * shows the position of a bond; $X_8$ is absent or —O—, —S—, —NHCO— or —CONH—; $m_3$ is an integer of 0 to 15; $n_5$ is an integer of 0 to 11; $n_6$ is an integer of 0 to 5; $X_7$ is absent or —O—, —S—, —COO—, —OCONH—, —NHCO— or —CONH—; $R_{12}$ is a hydrogen atom, a methyl group or an aliphatic hydrocarbon group having a carbon number of not less than 5; when a plurality of $X_7$ is present, respective $X_7$ may be the same or different; and when a plurality of $R_{12}$ is present, respective $R_{12}$ may be the same or different.

As the "aliphatic hydrocarbon group having a carbon number of not less than 5" for $R_{12}$, the "aliphatic hydrocarbon group" of the above-mentioned "organic group having an aliphatic hydrocarbon group" having a carbon number of not less than 5 can be mentioned, preferably one having a carbon number of 5 to 80.

In the formula (e), a group wherein $X_8$ is —O—; $m_3$ is 2 or 3; $n_5$ is 1; $n_6$ is 2 or 3; $X_7$ is —O—; and $R_{12}$ in the number of $m_3$ are each independently an alkyl group having a carbon number of 8 to 60, is preferable.

In the formula (e), a group wherein $X_8$ is —O—, $m_3$ is 2 or 3, $n_5$ is 1, $n_6$ is 3, $X_7$ in the number of $m_3$ is —O—, and $R_{12}$ in the number of $m_3$ are each independently an alkyl group having a carbon number of 14 to 30, is particularly preferable.

Specific examples of the "organic group having an aliphatic hydrocarbon group" from among aliphatic carbon chain groups having a carbon number of 18 or 22 include the following. In each group, * shows the position of a bond.

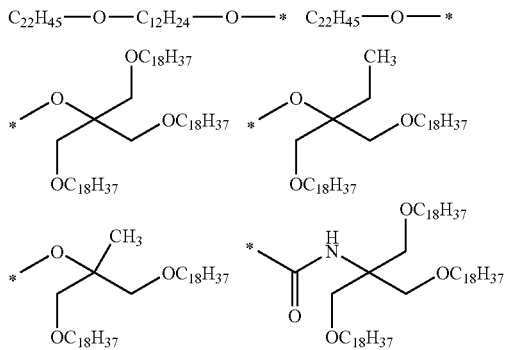

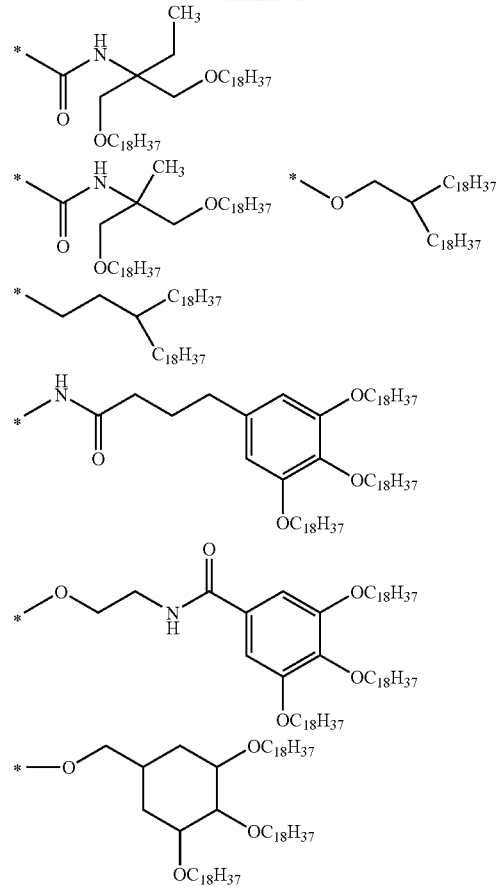

In addition, the following group is also used.

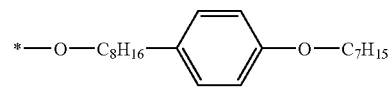

In the present specification, "the divalent organic group having an aliphatic hydrocarbon group" is a divalent organic group having an aliphatic hydrocarbon group in a molecule structure thereof.

As the "aliphatic hydrocarbon group" of the "divalent organic group having an aliphatic hydrocarbon group", those similar to the "aliphatic hydrocarbon group" of the above-mentioned "organic group having an aliphatic hydrocarbon group" can be mentioned.

A fluorene compound wherein 2 to 20 divalent unit structures derived from a compound represented by the formula (I) are connected via the "divalent organic group having an aliphatic hydrocarbon group" is also within the range of the present invention.

Examples of such divalent organic group include those represented by the following formula (i):

(i)

wherein Xa is absent, or —O—, —S—, —NHCO— or —CONH—; Rd is an aliphatic hydrocarbon group having a carbon number of not less than 5; $k_1$ is an integer of 1 to 10; when a plurality of Rd is present, respective Rd may be the same or different; and when a plurality of Xa is present, respective Xa may be the same or different, and represented by the following formula (ii):

  (ii)

wherein Re is an aliphatic hydrocarbon group having a carbon number of 5 to 60; $k_2$ is an integer of 1 to 3; and when Re is present in plurality, respective Re may be the same or different, are more preferable.

As the "aliphatic hydrocarbon group having a carbon number of not less than 5" for Rd, the "aliphatic hydrocarbon group" of the above-mentioned "organic group having an aliphatic hydrocarbon group" having a carbon number of not less than 5 can be mentioned.

As the "aliphatic hydrocarbon group having a carbon number of 5 to 60" for Re, the "aliphatic hydrocarbon group" of the above-mentioned "organic group having an aliphatic hydrocarbon group" having a carbon number of 5 to 60 can be mentioned.

As a fluorene compound represented by the formula (I) of the present invention, a compound represented by the formula (I') is preferable, more preferably a compound represented by the formula (I'), wherein ring A is a benzene ring; Y is a hydroxyl group, a bromo group or a chloro group; Ra is a halogen atom; an organic group having an aliphatic hydrocarbon group is a group represented by the formula (a) wherein $m_1$ is 1; $X_1$ is —O—; $R_1$ is an aliphatic hydrocarbon group having a carbon number of 5 to 60, a group represented by the formula (b) wherein $X_2$, $X_2'$, $X_2''$ and $X_2'''$ are each —O—; $R_2$ and $R_4$ are each independently an aliphatic hydrocarbon group having a carbon number of 5 to 60; $R_3$ is an organic group having an aliphatic hydrocarbon group having a carbon number 5 to 60; $n_1$, $n_2$, $n_3$ and $n_4$ are each 1; and $m_2$ is 1, or a group represented by the formula (e) wherein $X_8$ is —O—; $m_3$ is 2 or 3; $n_5$ is 1; $n_6$ is 3; $X_7$ is —O—; $R_{12}$ in the number of $m_3$ are each independently an alkyl group having a carbon number of 14 to 30, each of which formulas is present at the 2-position and/or the 7-position of the fluorene compound.

A fluorene compound represented by the formula (II) of the present invention is preferably a compound represented by the formula (II), wherein ring A is a benzene ring; Y is a hydroxyl group, a bromo group or a chloro group; n is 1; ring A has a halogen atom as the electron-withdrawing group; Rc' is a group represented by the formula (i) wherein Xa is —O—; Rd is an aliphatic hydrocarbon group having a carbon number of 5 to 60, and $k_1$ is an integer of 1 to 3.

Preferable examples of the fluorene compound of the present invention include the following fluorene compounds.
2-docosyloxy-9-(4-chlorophenyl)-9-fluorenol;
2-docosyloxy-9-(4-chlorophenyl)-9-bromofluorene;
2,7-didocosyloxy-9-(4-chlorophenyl)-9-bromofluorene;
2-(12-docosyloxy-dodecanoxy)-9-(3-fluorophenyl)-9-bromofluorene;
1,12-bis-[12-(2'-O-9-(4-chlorophenyl)-9-fluorenol)-dodecyloxy]-dodecane;
1,12-bis-[12-(2'-O-9-(4-chlorophenyl)-9-bromofluorene)-dodecyloxy]-dodecane;
2-(3-octadecyloxy-2,2-bis-octadecyloxymethyl-propoxy)-9-(4-chlorophenyl)-9-fluorenol;
2-(3-octadecyloxy-2,2-bis-octadecyloxymethyl-propoxy)-9-(4-chlorophenyl)-9-bromofluorene;
9-(4-chlorophenyl)-2-(3,4,5-tris(octadecyloxy)-cyclohexylmethoxy)-9-fluorenol; and 9-(4-chlorophenyl)-2-(3,4,5-tris(octadecyloxy)-cyclohexylmethoxy)-9-bromofluorene.

2. Production Method of the Compound of the Present Invention

While the production method of the compounds of the present invention is not particularly limited, for example, it can be synthesized by the following reactions.

Unless particularly specified, the starting material compounds may be a commercially available product, or can be produced according to a method known per se or a method analogous thereto.

While the yield of the compound obtained by each of the following methods may vary depending on the reaction conditions employed, these resultant products can be isolated and purified by a general method (recrystallization, column chromatography and the like), and then precipitated by a method of changing the solution temperature, a method of changing the solution composition and the like.

In each reaction, when the starting material compound has a hydroxy group, an amino group, a carboxy group or a carbonyl group, a protecting group generally used in the peptide chemistry and the like may be introduced into these groups, and the object compound can be obtained by removing the protecting group as necessary after the reaction.

Examples of the hydroxyl-protecting group include ($C_1$-$C_6$)alkyl group (e.g., methyl, ethyl, propyl, isopropyl, butyl, tert-butyl), phenyl group, trityl group, ($C_7$-$C_{10}$)aralkyl group (e.g., benzyl), formyl group, ($C_1$-$C_6$)alkyl-carbonyl group (e.g., acetyl, propionyl), benzoyl group, ($C_7$-$C_{10}$)aralkyl-carbonyl group (e.g., benzylcarbonyl), 2-tetrahydropyranyl group, 2-tetrahydrofuranyl group, silyl group (e.g., trimethylsilyl, triethylsilyl, dimethylphenylsilyl, tert-butyldimethylsilyl, tert-butyldiethylsilyl), ($C_2$-$C_6$)alkenyl group (e.g., 1-allyl) and the like. These groups are optionally substituted by 1 to 3 substituents selected from a halogen atom (e.g., fluorine, chlorine, bromine, iodine), a ($C_1$-$C_6$)alkyl group (e.g., methyl, ethyl, propyl), a ($C_1$-$C_6$)alkoxy group (e.g., methoxy, ethoxy, propoxy), a nitro group and the like.

Examples of the amino-protecting group include formyl group, ($C_1$-$C_6$)alkyl-carbonyl group (e.g., acetyl, propionyl), ($C_1$-$C_6$)alkoxy-carbonyl group (e.g., methoxycarbonyl, ethoxycarbonyl, tert-butoxycarbonyl), benzoyl group, ($C_7$-$C_{10}$)aralkyl-carbonyl group (e.g., benzylcarbonyl), ($C_7$-$C_{14}$) aralkyloxy-carbonyl group (e.g., benzyloxycarbonyl, 9-fluorenylmethoxycarbonyl), trityl group, phthaloyl group, N,N-dimethylaminomethylene group, silyl group (e.g., trimethylsilyl, triethylsilyl, dimethylphenylsilyl, tert-butyldimethylsilyl, tert-butyldiethylsilyl), ($C_2$-$C_6$)alkenyl group (e.g., 1-allyl) and the like. These groups are optionally substituted by 1 to 3 substituents selected from a halogen atom (e.g., fluorine, chlorine, bromine, iodine), a ($C_1$-$C_6$) alkoxy group (e.g., methoxy, ethoxy, propoxy), a nitro group and the like.

Examples of the carboxy-protecting group include ($C_1$-$C_6$) alkyl group (e.g., methyl, ethyl, propyl, isopropyl, butyl, tert-butyl), ($C_7$-$C_{10}$)aralkyl group (e.g., benzyl), phenyl group, trityl group, silyl group (e.g., trimethylsilyl, triethylsilyl, dimethylphenylsilyl, tert-butyldimethylsilyl, tert-butyldiethylsilyl, tert-butyldiphenylsilyl), ($C_2$-$C_6$)alkenyl group (e.g., 1-allyl) and the like can be mentioned. These groups are optionally substituted by 1 to 3 substituents selected from a halogen atom (e.g., fluorine, chlorine, bromine, iodine), a ($C_1$-$C_6$)alkoxy group (e.g., methoxy, ethoxy, propoxy), a nitro group and the like.

Examples of the carbonyl-protecting group include cyclic acetal (e.g., 1,3-dioxane), acyclic acetal (e.g., di-($C_1$-$C_6$) alkylacetal) and the like.

These protecting groups can be removed by a method known per se, for example, the method described in Protective Groups in Organic Synthesis, John Wiley and Sons (1980) and the like. For example, a method using acid, base, ultraviolet rays, hydrazine, phenylhydrazine, sodium N-methyldithiocarbamate, tetrabutylammonium fluoride, palladium acetate, trialkylsilylhalide (e.g., trimethylsilyliodide, trimethylsilylbromide and the like) and the like, a reduction method and the like are used.

Production Method

An example wherein at least any one of ring A, ring B and ring C (hereinafter also to be referred simply as a ring) is substituted by an organic group having an aliphatic hydrocarbon group via —O— is shown in the following.

In this method, as the "aliphatic hydrocarbon group", those similar to the "aliphatic hydrocarbon group" of the above-mentioned "organic group having an aliphatic hydrocarbon group" can be mentioned.

Step 1.

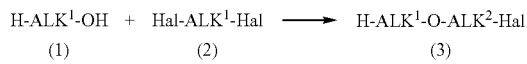

wherein Hal is a halogen atom (chlorine atom, bromine atom, iodine atom, fluorine atom; preferably bromine atom), and ALK$^1$ and ALK$^2$ are the same or different and each is an aliphatic hydrocarbon group.

Compound (1) is reacted with 0.2 to 5 molar equivalents of compound (2) to give compound (3). Generally, the reaction is performed in the presence of a base in a solvent that does not adversely influence the reaction.

Examples of the base include an alkali metal salt such as potassium hydroxide, sodium hydroxide, sodium hydrogen carbonate, potassium carbonate and the like; amine such as pyridine, triethylamine, N,N-dimethylaniline, 1,8-diazabicyclo[5.4.0]undec-7-en and the like; metal hydride such as potassium hydride, sodium hydride and the like; alkali metal alkoxide such as sodium methoxide, sodium ethoxide, potassium tert-butoxide and the like, and the like.

The amount of the base to be used is preferably about 1 to 5 molar equivalents relative to compound (1).

As such solvent, halogenated hydrocarbon such as chloroform, dichloromethane and the like; and nonpolar organic solvent such as 1,4-dioxane, tetrahydrofuran and the like can be mentioned. These solvents may be used in a mixture of two or more kinds at an appropriate ratio. It is preferably tetrahydrofuran. The amount of the solvent to be used is generally 2- to 50-fold volume relative to compound (1).

The reaction temperature is generally 20° C. to 150° C., preferably 50° C. to 100° C. The reaction time is generally 1 to 30 hours.

Step 2.

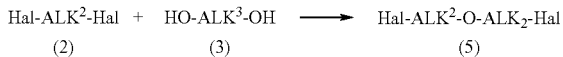

wherein Hal is a halogen atom (chlorine atom, bromine atom, iodine atom, fluorine atom; preferably bromine atom), and ALK$^2$ and ALK$^3$ are the same or different and each is an aliphatic hydrocarbon group.

Compound (4) is reacted with about 0.3 to 5 molar equivalents of compound (2) to give compound (5). Generally, the reaction is performed in the presence of a base in a solvent that does not adversely influence the reaction.

Examples of the base include an alkali metal salt such as potassium hydroxide, sodium hydroxide, sodium hydrogen carbonate, potassium carbonate and the like; amine such as pyridine, triethylamine, N,N-dimethylaniline, 1,8-diazabicyclo[5.4.0]undec-7-en and the like; metal hydride such as potassium hydride, sodium hydride and the like; alkali metal alkoxide such as sodium methoxide, sodium ethoxide, potassium tert-butoxide and the like, and the like.

The amount of the base to be used is preferably about 1 to 10 molar equivalents relative to compound (4).

As such solvent, halogenated hydrocarbon such as chloroform, dichloromethane and the like; and nonpolar organic solvent such as 1,4-dioxane, tetrahydrofuran and the like can be mentioned. These solvents may be used in a mixture of two or more kinds at an appropriate ratio. It is preferably tetrahydrofuran. The amount of the solvent to be used is generally 2- to 50-fold volume relative to compound (2).

The reaction temperature is generally 20° C. to 150° C., preferably 50° C. to 100° C. The reaction time is generally 1 to 30 hours.

Step 3-1.

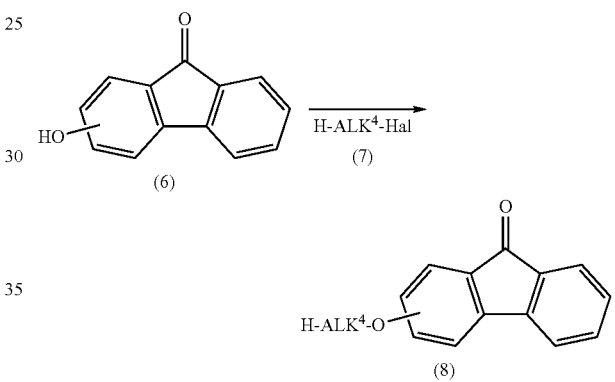

wherein Hal is a halogen atom (chlorine atom, bromine atom, iodine atom, fluorine atom; preferably bromine atom) and ALK$^4$ is an aliphatic hydrocarbon group.

Compound (6) is reacted with 0.3 to 5 molar equivalents of compound (7) to give compound (8). Generally, the reaction is performed in the presence of a base in a solvent that does not adversely influence the reaction.

Examples of the base include an alkali metal salt such as potassium hydroxide, sodium hydroxide, sodium hydrogen carbonate, potassium carbonate and the like; amine such as pyridine, triethylamine, N,N-dimethylaniline, 1,8-diazabicyclo[5.4.0]undec-7-en and the like; metal hydride such as potassium hydride, sodium hydride and the like; alkali metal alkoxide such as sodium methoxide, sodium ethoxide, potassium tert-butoxide and the like, and the like.

The amount of the base to be used is preferably about 1 to 5 molar equivalents relative to compound (6).

Examples of the solvent include aromatic hydrocarbon such as benzene, toluene, xylene and the like; nitrile such as acetonitrile, propionitrile and the like; ether such as tetrahydrofuran, 1,4-dioxane, diethyl ether and the like; ketone such as acetone, 2-butanone and the like; halogenated hydrocarbon such as chloroform, dichloromethane and the like; amide such as N,N-dimethylformamide and the like; sulfoxide such as dimethyl sulfoxide and the like, and the like. These solvents may be used in a mixture of two or more kinds at an appropriate ratio. It is preferably dimethylformamide. The amount of the solvent to be used is generally 2- to 50-fold volume relative to compound (6).

The reaction temperature is generally 30° C. to 150° C., preferably 50° C. to 100° C. The reaction time is generally 1 to 30 hours.

Step 3-2.

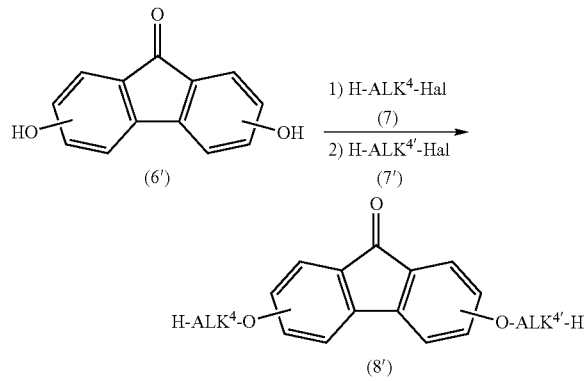

wherein Hal is a halogen atom (chlorine atom, bromine atom, iodine atom, fluorine atom; preferably bromine atom) and $ALK^4$ and $ALK^{4'}$ are the same or different and each is an aliphatic hydrocarbon group.

Compound (6') is reacted with halide to give compound (8'). When compound (7) and compound (7') are the same, the above-mentioned reaction can be performed in one step. When compound (7) and compound (7') are different compounds, compound (6') is reacted with 0.3 to 5 molar equivalents of compound (7) and then reacted with 0.3 to 5 molar equivalents of compound (7'). During reaction with compound (7), the moiety to be reacted with compound (7') is preferably protected with a protecting group in advance. As the protecting group, hydroxyl-protecting group can be mentioned and, for example, $(C_1-C_6)$alkyl group (e.g., methyl, ethyl, propyl, isopropyl, butyl, tert-butyl), phenyl group, trityl group, $(C_7-C_{10})$aralkyl group (e.g., benzyl), formyl group, $(C_1-C_6)$alkyl-carbonyl group (e.g., acetyl, propionyl), benzoyl group, $(C_7-C_{10})$aralkyl-carbonyl group (e.g., benzylcarbonyl), 2-tetrahydropyranyl group, 2-tetrahydrofuranyl group, silyl group (e.g., trimethylsilyl, triethylsilyl, dimethylphenylsilyl, tert-butyldimethylsilyl, tert-butyldiethylsilyl), $(C_2-C_6)$alkenyl group (e.g., 1-allyl) and the like can be mentioned.

These reactions are generally performed in the presence of a base in a solvent that does not adversely influence the reaction.

Examples of the base include an alkali metal salt such as potassium hydroxide, sodium hydroxide, sodium hydrogen carbonate, potassium carbonate and the like; amine such as pyridine, triethylamine, N,N-dimethylaniline, 1,8-diazabicyclo[5.4.0]undec-7-en and the like; metal hydride such as potassium hydride, sodium hydride and the like; alkali metal alkoxide such as sodium methoxide, sodium ethoxide, potassium tert-butoxide and the like, and the like.

The amount of the base to be used is preferably about 1 to 10 molar equivalents relative to compound (6').

Examples of the solvent include aromatic hydrocarbon such as benzene, toluene, xylene and the like; nitrile such as acetonitrile, propionitrile and the like; ether such as tetrahydrofuran, 1,4-dioxane, diethyl ether and the like; ketone such as acetone, 2-butanone and the like; halogenated hydrocarbon such as chloroform, dichloromethane and the like; amide such as N,N-dimethylformamide and the like; sulfoxide such as dimethyl sulfoxide and the like, and the like. These solvents may be used in a mixture of two or more kinds at an appropriate ratio. It is preferably dimethylformamide. The amount of the solvent to be used is generally 2- to 50-fold volume relative to compound (6').

The reaction temperature is generally 30° C. to 150° C., preferably 50° C. to 100° C. The reaction time is generally 1 to 70 hours.

Step 3-3.

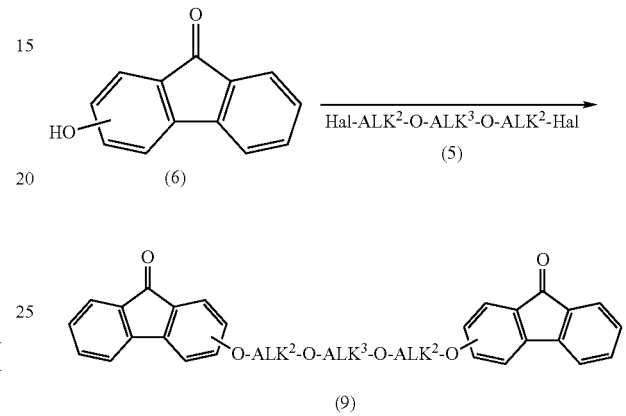

wherein Hal is a halogen atom (chlorine atom, bromine atom, iodine atom, fluorine atom; preferably bromine atom) and $ALK^2$ and $ALK^3$ are the same or different and each is an aliphatic hydrocarbon group.

Compound (6) reacted with about 0.5 to 5 molar equivalents of compound (5) to give compound (9). Generally, the reaction is performed in the presence of a base in a solvent that does not adversely influence the reaction.

Examples of the base include an alkali metal salt such as potassium hydroxide, sodium hydroxide, sodium hydrogen carbonate, potassium carbonate and the like; amine such as pyridine, triethylamine, N,N-dimethylaniline, 1,8-diazabicyclo[5.4.0]undec-7-en and the like; metal hydride such as potassium hydride, sodium hydride and the like; alkali metal alkoxide such as sodium methoxide, sodium ethoxide, potassium tert-butoxide and the like, and the like.

The amount of the base to be used is preferably about 1 to 10 molar equivalents relative to compound (6).

Examples of the solvent include aromatic hydrocarbon such as benzene, toluene, xylene and the like; nitrile such as acetonitrile, propionitrile and the like; ether such as tetrahydrofuran, 1,4-dioxane, diethyl ether and the like; ketone such as acetone, 2-butanone and the like; halogenated hydrocarbon such as chloroform, dichloromethane and the like; amide such as N,N-dimethylformamide and the like; sulfoxide such as dimethyl sulfoxide and the like, and the like. These solvents may be used in a mixture of two or more kinds at an appropriate ratio. It is preferably dimethylformamide. The amount of the solvent to be used is generally 2- to 50-fold volume relative to compound (6).

The reaction temperature is generally 30° C. to 150° C., preferably 50° C. to 100° C. The reaction time is generally 1 to 70 hours.

Step 4.

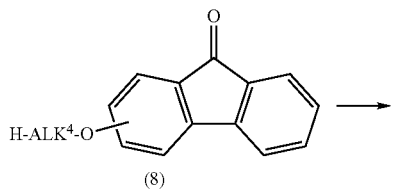

(8)

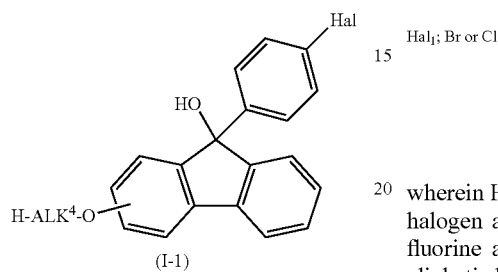

(I-1)

wherein Hal is a halogen atom (chlorine atom, bromine atom, iodine atom, fluorine atom; preferably chlorine atom), and ALK⁴ is an aliphatic hydrocarbon group.

Compound (8) is reacted with a Grignard reagent generally in a solvent that does not adversely influence the reaction to give compound (I-1).

As the Grignard reagent used in this step, 4-chlorophenylmagnesium bromide, 3-chlorophenylmagnesium bromide, 3-trifluoromethylphenylmagnesium bromide, 3-fluorophenylmagnesium bromide, 3,5-difluorophenylmagnesium bromide and the like can be mentioned.

The amount of the Grignard reagent to be used is preferably about 1 to 10 molar equivalents relative to compound (8).

As such solvent, halogenated hydrocarbon such as chloroform, dichloromethane and the like; and nonpolar organic solvent such as 1,4-dioxane, tetrahydrofuran and the like can be mentioned. These solvents may be used in a mixture of two or more kinds at an appropriate ratio. It is preferably tetrahydrofuran. The amount of the solvent to be used is generally 2- to 50-fold volume relative to compound (8).

The reaction temperature is generally 10° C. to 100° C., preferably 30° C. to 70° C. The reaction time is generally 1 to 30 hours.

Step 5.

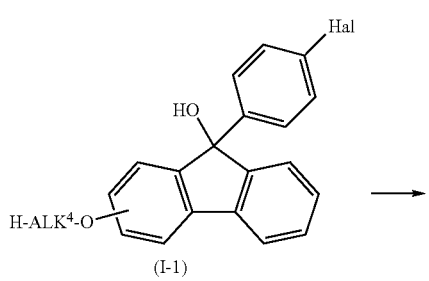

(I-1)

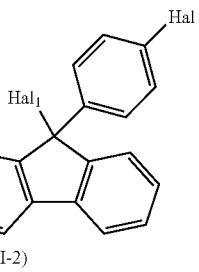

(I-2)

Hal₁; Br or Cl wherein Hal₁ is a bromine atom or a chlorine atom, Hal is a halogen atom (chlorine atom, bromine atom, iodine atom, fluorine atom; preferably chlorine atom) and ALK⁴ is an aliphatic hydrocarbon group.

Compound (I-1) is reacted with a halogenating agent generally in a solvent that does not adversely influence the reaction to give compound (I-2).

As the halogenating agent to be used in this step, acetyl bromide, acetyl chloride, thionyl chloride, thionyl bromide, PBr₃, HBr, NBS and the like can be mentioned.

The amount of halogenated acyl to be used is preferably about 1 to 30 molar equivalents relative to compound (I-1).

As such solvent, halogenated hydrocarbon such as chloroform, dichloromethane and the like; and nonpolar organic solvent such as 1,4-dioxane, tetrahydrofuran and the like can be mentioned. These solvents may be used in a mixture of two or more kinds at an appropriate ratio. It is preferably chloroform. The amount of the solvent to be used is generally 2- to 50-fold volume relative to compound (I-1).

The reaction temperature is generally 10° C. to 100° C., preferably 50° C. to 80° C. The reaction time is generally 1 to 70 hours.

Compound (I-3) can be obtained by successively performing the reactions in step 4 and step 5 using compound (3) obtained in step 1 instead of compound (7) in step 3-1.

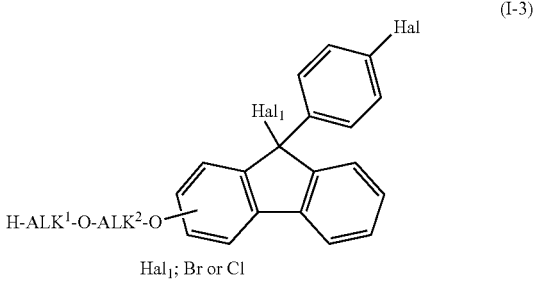

(I-3)

Hal₁; Br or Cl wherein Hal₁ is a bromine atom or a chlorine atom, Hal is a halogen atom (chlorine atom, bromine atom, iodine atom, fluorine atom; preferably fluorine atom), and ALK¹ and ALK² are the same or different and each is an aliphatic hydrocarbon group.

Step 6.

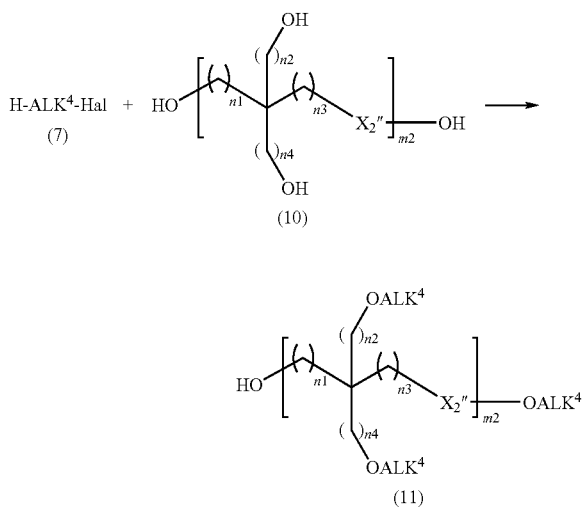

(11)

wherein Hal is a halogen atom (chlorine atom, bromine atom, iodine atom, fluorine atom; preferably fluorine atom), $ALK^4$ is an aliphatic hydrocarbon group, $X_2''$ in the number of $m_2$ are each independently absent, or —O—, —S—, —NHCO— or —CONH—, $n_1$, $n_2$, $n_3$ and $n_4$ are each independently an integer of 0 to 2, and $m_2$ is an integer of 1 or 2, when a plurality of $n_1$, $n_2$, $n_3$ and $n_4$ are each present, each respective $n_1$, $n_2$, $n_3$ and $n_4$ may be the same or different, and when a plurality of $ALK^4$ is present, to respective $ALK^4$ may be the same or different.

Compound (7) is reacted with 0.2 to 5 molar equivalents of compound (10) to give compound (11). Generally, the reaction is performed in the presence of a base in a solvent that does not adversely influence the reaction.

Examples of the base include an alkali metal salt such as potassium hydroxide, sodium hydroxide, sodium hydrogen carbonate, potassium carbonate and the like; amine such as pyridine, triethylamine, N,N-dimethylaniline, 1,8-diazabicyclo[5.4.0]undec-7-en and the like; metal hydride such as potassium hydride, sodium hydride and the like; alkali metal alkoxide such as sodium methoxide, sodium ethoxide, potassium tert-butoxide and the like, and the like.

The amount of the base to be used is preferably about 1 to 5 molar equivalents relative to compound (7).

Examples of the solvent include aromatic hydrocarbon such as benzene, toluene, xylene and the like; nitrile such as acetonitrile, propionitrile and the like; ether such as tetrahydrofuran, 1,4-dioxane, diethyl ether and the like; ketone such as acetone, 2-butanone and the like; halogenated hydrocarbon such as chloroform, dichloromethane and the like; amide such as N,N-dimethylformamide and the like; sulfoxide such as dimethyl sulfoxide and the like, and the like. These solvents may be used in a mixture of two or more kinds at an appropriate ratio. It is preferably dimethylformamide. The amount of the solvent to be used is generally 2- to 50-fold volume relative to compound (7).

The reaction temperature is generally 20° C. to 150° C., preferably 50° C. to 100° C. The reaction time is generally 1 to 30 hours.

Step 7.

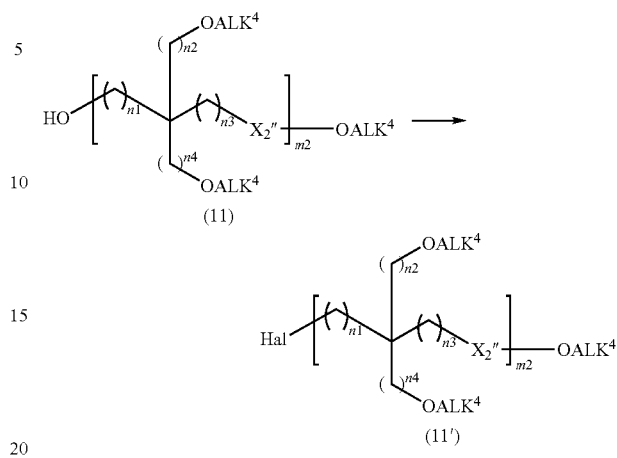

wherein Hal is a halogen atom (chlorine atom, bromine atom, iodine atom, fluorine atom; preferably iodine atom), $ALK^4$ is an aliphatic hydrocarbon group, $X_2''$ in the number of $m_2$ are each independently absent, or —O—, —S—, —NHCO— or —CONH—, $n_1$, $n_2$, $n_3$ and $n_4$ are each independently an integer of 0 to 2, and $m_2$ is an integer of 1 or 2, when a plurality of $n_1$, $n_2$, $n_3$ and $n_4$ are each present, each respective $n_1$, $n_2$, $n_3$ and $n_4$ may be the same or different, and when a plurality of $ALK^4$ is present, respective $ALK^4$ may be the same or different.

A hydroxyl group of compound (11) is substituted by halogen to give compound (11').

Triphenylphosphine and a halogen source are reacted in a solvent that does not adversely influence the reaction. Generally, the reaction is preferably performed in the presence of imidazole. As the halogen source, carbon tetrachloride, hexachloroacetone and triphosgene (chlorine source), carbon tetrabromide (bromine source), iodomethane and iodine (iodine source) and the like can be mentioned. The amount of triphenylphosphine to be used is preferably about 0.1-5 molar equivalents relative to compound (11), and the amount of the halogen source to be used is about 1 to 5 molar equivalents relative to compound (11). When imidazole is used, the amount thereof to be used is about 0.1 to 5 molar equivalents relative to compound (11).

Examples of the solvent include aromatic hydrocarbon such as benzene, toluene, xylene and the like; nitrile such as acetonitrile, propionitrile and the like; ether such as tetrahydrofuran, 1,4-dioxane, diethyl ether and the like; ketone such as acetone, 2-butanone and the like; halogenated hydrocarbon such as chloroform, dichloromethane and the like; amide such as N,N-dimethylformamide and the like; sulfoxide such as dimethyl sulfoxide and the like, and the like. These solvents may be used in a mixture of two or more kinds at an appropriate ratio. It is preferably toluene. The amount of the solvent to be used is generally 3-50-fold volume relative to compound (11).

The reaction temperature is generally 30° C. to 150° C., preferably 40° C. to 120° C. The reaction time is generally 0.5 to 24 hours.

Compound (11) and compound (11') produced via step 6 and step 7 can be a useful intermediate to produce the compound of the present invention.

Using compounds (11) and (11') obtained in step 6 and step 7, an intermediate useful for producing the compound of the present invention can be obtained by performing the reactions of the above-mentioned step 3-1, step 3-2 and/or step 3-3.

One example is shown in the following. In the scheme, the carbon number of aliphatic hydrocarbon group, the kind of halogen atom, reaction reagent and the like are shown for convenience, and can be appropriately changed within the range of the above-mentioned definitions.
Ts: tosyl group,
Ph: phenyl group,
Py: pyridine,
Et: ethyl group

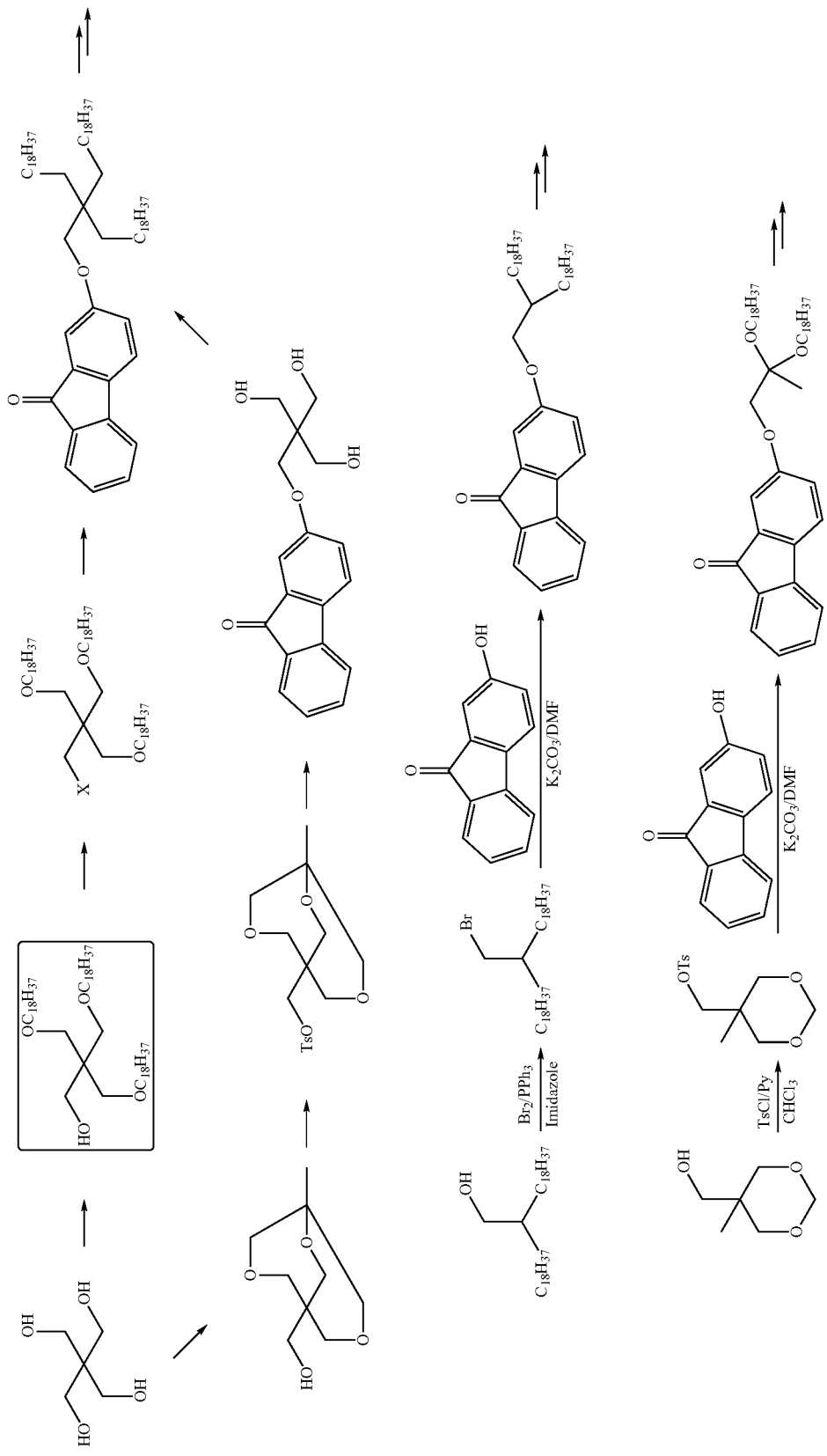

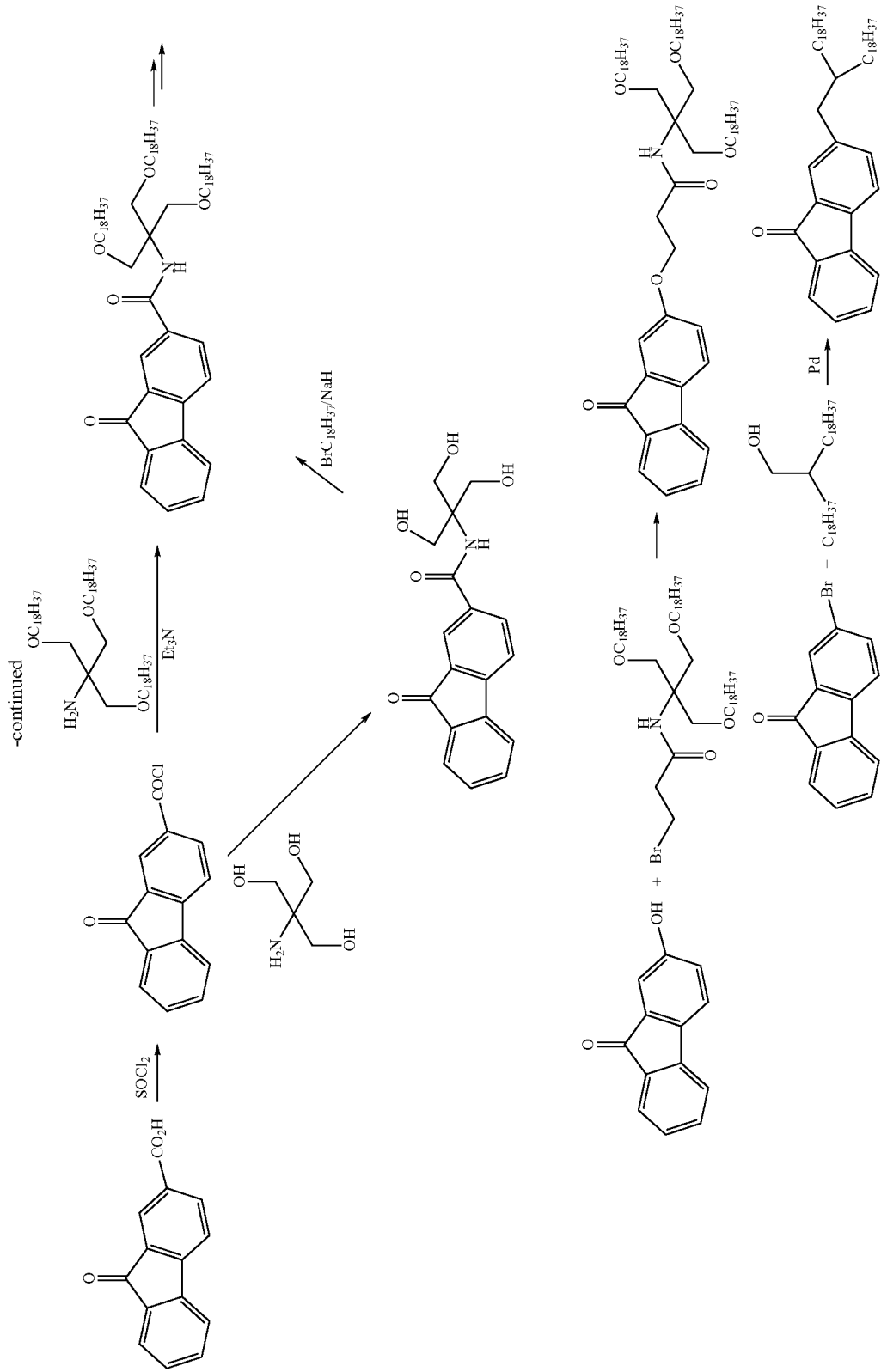

wherein X is a halogen atom (chlorine atom, bromine atom, iodine atom, fluorine atom).

In addition, even when "an organic group having an aliphatic hydrocarbon group" is the following formula (d):

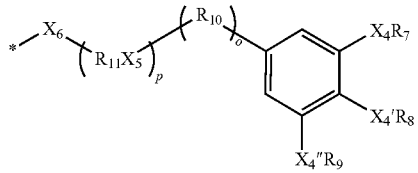

wherein each symbol is as defined above, an intermediate useful for producing the compound of the present invention can be obtained by performing the reactions of the above-mentioned step 3-1, step 3-2 and/or step 3-3. One example is shown in the following. In the scheme, the carbon number of aliphatic hydrocarbon group, the kind of halogen atom, reaction reagent and the like are shown for convenience, and can be appropriately changed within the range of the above-mentioned definitions.

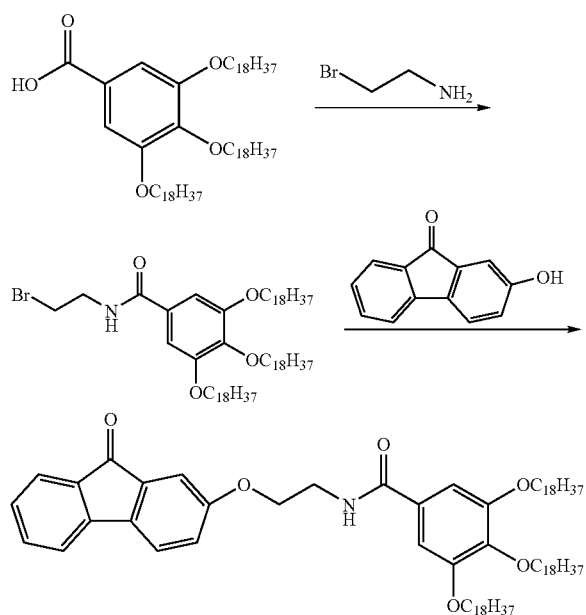

In addition, even when "an organic group having an aliphatic hydrocarbon group" is the following formula (e):

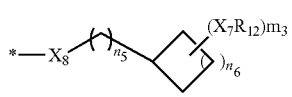

wherein each symbol is as defined above, an intermediate useful for producing the compound of the present invention can be obtained by performing the reactions of the above-mentioned step 3-1, step 3-2 and/or step 3-3. One example is shown in the following. In the scheme, the carbon number of aliphatic hydrocarbon group, the kind of halogen atom, reaction reagent and the like are shown for convenience, and can be appropriately changed within the range of the above-mentioned definitions.

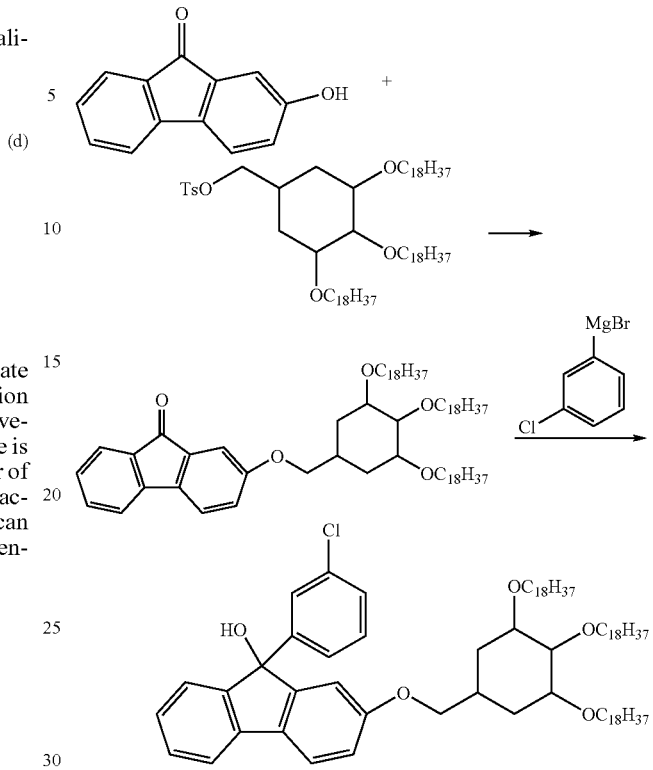

When a compound wherein an organic group having an aliphatic hydrocarbon group substitutes a ring via a group other than —O— is to be produced, the compound of the present invention can be produced according to the above-mentioned method, or by appropriately changing the above-mentioned method. Such change can be made by performing a reaction generally performed in the art. For example, an organic group having an aliphatic hydrocarbon group substitutes a ring via —NH— can be obtained by dehydrative condensation of a compound having a carboxyl group on end and a compound having an amino group on end.

3. Organic Synthesis Reaction Method

The compound of the present invention can be used as a protecting reagent for various organic synthesis reactions. For example, the following steps are performed.

(i) a step of binding the compound of the present invention to amino acid or peptide (binding step), and (ii) a step of precipitating the bonded product of the compound and the amino acid or peptide obtained in the above-mentioned step (precipitation step).

First, the compound of the present invention is dissolved in a soluble solvent, then a reaction substrate to be reacted (amino acid or peptide to be a material for peptide synthesis here) is added to a reagent dissolved in a soluble solvent to bind the both (binding step). As a solvent to be used for the reaction system, a general organic solvent can be used. Since superior reactivity can be expected when the solubility in the solvent is higher, a solvent in which the compound of the present invention shows high solubility is preferably selected. Specifically, halogenated hydrocarbon such as chloroform, dichloromethane and the like; and a nonpolar organic solvent such as 1,4-dioxane, tetrahydrofuran and the like can be mentioned. These solvents may be used in a mixture of two or more kinds at an appropriate ratio. In addition, the above-mentioned halogenated hydrocarbons and nonpolar organic solvent may be mixed with aromatic hydrocarbon such as benzene, toluene, xylene and the like; nitrile such as acetonitrile, propionitrile and the like; ketone such as acetone, 2-butanone and the like; amide such as N,N-dimethylformamide and the like; sulfoxide such as dimethyl sulfoxide and the like at an appropriate ratio and used as long as the compound of the present invention is dissolved.

For confirmation of the progress of the reaction, a method similar to general liquid phase organic synthesis reaction can be applied. That is, thin layer silica gel chromatography, high performance liquid chromatography and the like can be used to track the reaction.

Step i (Binding Step)

In this step, the compound of the present invention dissolved in a soluble solvent is bonded to a reactive substrate.

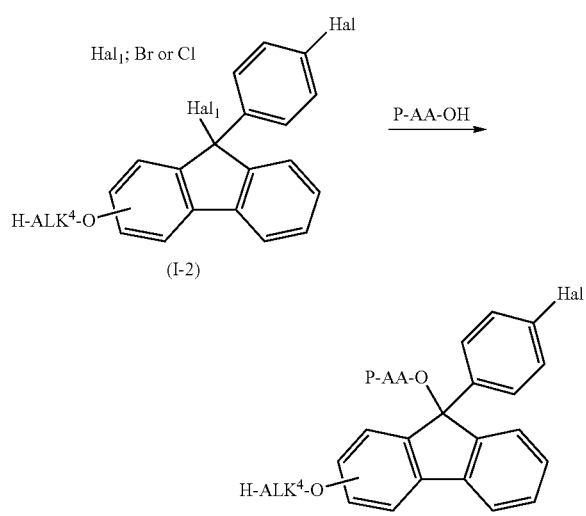

wherein $Hal_1$ is a bromine atom or a chlorine atom, Hal is a halogen atom (chlorine atom, bromine atom, iodine atom, fluorine atom; preferably fluorine atom), P is an amino-protecting group, AA is a group derived from amino acid, and $ALK^4$ is an aliphatic hydrocarbon group.

The compound of the present invention (I-2) is reacted with a protected amino acid (amino acid bound with a protecting group: P-AA-OH) generally in a solvent that does not adversely influence the reaction to give a compound (bonded product) wherein compound (I-2) is bound with protected amino acid. The amino acid of the "group derived from amino acid" is not particularly limited as long as it is intended to be bonded to compound (I-2), and may be natural amino acid or non-natural amino acid.

The compound of the present invention such as compound (I-2) and the like is bonded to amino acid or peptide to be a starting material and functions as an anchor in a peptide synthesis reaction.

While the protecting group of protected amino acid (corresponding to P in the above-mentioned scheme) varies, for example, by protection target amino acid, those generally used, specifically those similar to the above-mentioned groups can be recited as examples. When amino acid is alanine, P is preferably a benzyloxycarbonyl (Z) group or a 9-fluorenylmethoxycarbonyl (Fmoc) group.

The protected amino acid used in this step is of the same kind as the amino acid to be bonded to compound (I-2). For example, when alanine is to be bonded to (I-2), the protected amino acid is P-alanine.

The amount of protected amino acid to be used in this step is preferably about 1 to 10 molar equivalents relative to compound (I-2).

As such solvent, halogenated hydrocarbon such as chloroform, dichloromethane and the like; and nonpolar organic solvent such as 1,4-dioxane, tetrahydrofuran and the like can be mentioned. These solvents may be used in a mixture of two or more kinds at an appropriate ratio. It is preferably chloroform. The amount of the solvent to be used is generally 2- to 50-fold volume relative to compound (I-2).

The reaction temperature is generally 10° C. to 100° C., preferably 20° C. to 70° C. The reaction time is generally 1 to 70 hours.

When a compound of the present invention wherein Y is a hydroxyl group is used, the reaction substrate is a compound having an amino group, and when a compound of the present invention wherein Y is an amino group is used, the reaction substrate is a compound having a carboxyl group.

Step ii (Precipitation Step)

In this step, the solvent used to dissolve the bonded product obtained in the above-mentioned step is changed to cause precipitation to isolate the bonded product.

After the reaction, the solvent used to dissolve the compound is changed (e.g., change of solvent composition, change of solvent kind) to conveniently isolate the obtained bonded product by precipitation. That is, the bonded product is precipitated and impurity is eliminated by performing a reaction under conditions where the compound is dissolved, and changing the solvent after the reaction. Examples of the change of solvent include use of a halogen solvent, THF and the like for dissolution, and a polar organic solvent such as methanol, acetonitrile and the like for precipitation.

The bonded product isolated by precipitation is subjected to a desired reaction, and protecting reagent derived from the compound of the present invention is finally removed (deprotection step).

For removal of the protecting reagent, various methods generally used in the art, particularly in the peptide synthesis, are employed. Generally, a method including addition of an acid and the like is employed. As the acid, trifluoroacetic acid (TFA), hydrochloric acid, sulfuric acid, mesylic acid, tosylic acid, trifluoroethanol, hexafluoroisopropanol and the like are used. Among these, TFA is preferable.

The amount of the acid to be used is appropriately determined according to the kind of the acid, and an amount suitable for removing the protecting reagent is used. The reaction temperature is generally 0° C. to 80° C., preferably 10° C. to 50° C. The reaction time is generally 0.5 to 24 hours.

Peptide can be produced by liquid phase synthesis utilizing the above-mentioned steps. Specifically, the synthesis includes the following steps.

(1) a step of condensing the fluorene compound of the present invention with the C-terminal of N-protected amino acid or N-protected peptide to give C-fluorene compound-protected amino acid or C-fluorene compound-protected peptide (C-terminal fluorene compound protection step), (2) a step of removing the protecting group from the N-terminal of the amino acid or peptide obtained in the above-mentioned step (N-terminal deprotection step), (3) a step of condensing the N-terminal of the amino acid or peptide obtained in the above-mentioned step with N-protected amino acid or N-protected peptide (peptide chain elongation step), and (4) a step of precipitating the peptide obtained in the above-mentioned step (precipitation step).

Step 1 (C-Terminal Fluorene Compound Protection Step)

In this step, the fluorene compound of the present invention is condensed with the C-terminal of N-protected amino acid or N-protected peptide to give C-fluorene compound-protected amino acid or C-fluorene compound-protected peptide. For example, the step can be performed according to the above-mentioned binding step.

In the present invention, the "N-protected amino acid" and "N-protected peptide" mean amino acid and peptide wherein an amino group is protected and a carboxyl group is not protected, which can be indicated as "P-AA-OH" (P is an amino-protecting group).

The condensation reaction of the fluorene compound of the present invention with N-protected amino acid or N-protected peptide at the C-terminal is generally performed in a solvent that does not influence the reaction. For example, when Y is a halogen atom (e.g., a bromo group, a chloro group, an iodo group, preferably a bromo group and a chloro group), the reaction can be performed in the presence of a base. As the base, etheramine, ethylamine, trimethylamine, triethylamine, triethanolamine, diisopropylethylamine and the like can be mentioned. When Y is a hydroxyl group, the reaction can be performed in the presence of a condensing agent. Examples of the condensing agent include dicyclohexylcarbodiimide, diisopropylcarbodiimide, N-ethyl-N'-3-dimethylaminopropylcarbodiimide and hydrochloride thereof (EDC·HCl) and the like. Where necessary, a condensing agent may be used together with a promoter such as N-hydroxysuccinimide, 1-hydroxybenzotriazole (HOBt) and the like.

As the solvent to be used for this step, halogenated hydrocarbon such as chloroform, dichloromethane and the like; and nonpolar organic solvent such as 1,4-dioxane, tetrahydrofuran and the like can be mentioned. These solvents may be used in a mixture of two or more kinds at an appropriate ratio. It is preferably chloroform. The amount of the solvent to be used is generally 2- to 50-fold volume relative to the fluorene compound of the present invention.

The reaction temperature is generally 10° C. to 100° C., preferably 20° C. to 70° C. The reaction time is generally 1 to 70 hours.

Step 2 (N-Terminal Deprotection Step)

In this step, the protecting group at the N-terminal of the amino acid or peptide obtained in the above-mentioned step is removed.

Deprotection is appropriately selected according to the kind of the N-protecting group. A group that can be removed under conditions different from those for the removal of the protecting reagent derived from the compound of the present invention is preferable. For example, for an Fmoc group, it is removed by treating with a base. The reaction is generally performed in a solvent that does not influence the reaction.

As the base, dimethylamine, diethylamine and the like can be mentioned. Examples of the solvent include halogenated hydrocarbon such as chloroform, dichloromethane and the like; aromatic hydrocarbon such as toluene, xylene and the like; ether such as diethyl ether, tetrahydrofuran, dioxane and the like; nitrile such as acetonitrile and the like, and a mixture thereof can be mentioned.

Step 3 (Peptide Chain Elongation Step)

In this step, the N-terminal of amino acid or peptide deprotected in step 2 is condensed with N-protected amino acid or N-protected peptide.

This step is performed according to the method of the above-mentioned step 1 wherein Y is a hydroxyl group.

Step 4 (Precipitation Step)

This step is performed in the same manner as in the precipitation step in the above-mentioned step ii.

In the method of producing a peptide of the present invention, N-protected amino acid or protected peptide obtained in step 4 can be subjected to a desired number of repeats of steps (5)-(7).

(5) a step of deprotecting the N-terminal of the peptide obtained in the precipitation step, (6) a step of condensing the N-terminal of peptide obtained in the above-mentioned step with N-protected amino acid or N-protected peptide, and (7) a step of precipitating the peptide obtained in the above-mentioned step.

Step 5

This step is performed in the same manner as in the N-terminal deprotection step of step 2.

Step 6

This step is performed in the same manner as in the peptide chain elongation step of step 3.

Step 7

This step is performed in the same manner as in the precipitation step of step ii.

The method of producing a peptide of the present invention can further comprise, after the precipitation step of step 4 or step 7, a step of deprotecting the C-terminal of peptide which is protected with a fluorene compound. For example, the step is performed according to the step of removing the protecting reagent of the present invention mentioned above.

4. Kit for Liquid Phase Synthesis of Peptide

The present invention also provides a kit for liquid phase synthesis of peptide, which contains the above-mentioned compound of the present invention as an essential constituent component. The kit may contain, besides the compound of the present invention, other components necessary for liquid phase synthesis reaction of peptide, for example, various solvents used for the reaction, amino acid (or peptide) to be the starting material and the like. When desired, a manual of liquid phase synthesis of peptide using the compound of the present invention can also be attached.

Other features of the invention will become apparent in the course of the following descriptions of exemplary embodiments which are given for illustration of the invention and are not intended to be limiting thereof.

EXAMPLES

The reagents, apparatuses and materials used in the present invention are commercially available unless otherwise specified. In the present specification, when amino acid and the like are indicated by abbreviation, each indication is based on the abbreviation of the IUPAC-IUB Commission on Biochemical Nomenclature or conventional abbreviations in the art.

Example 1

1-1: Synthesis of 2-docosyloxy-9-fluorenone

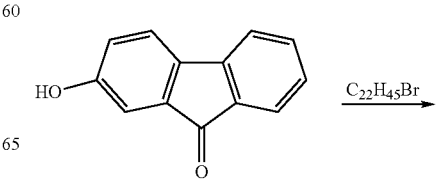

-continued

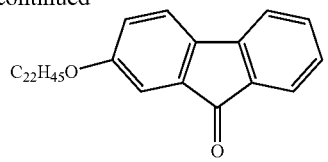

2-Hydroxy-9-fluorenone (196 mg, 2.04 mmol) was dissolved in DMF (8 ml), potassium carbonate (423 mg, 3.06 mmol), and docosyl bromide (96%, 785 mg, 1.93 mmol) were added. The mixture was heated to 80° C. and stirred overnight. After completion of the reaction, the reaction mixture was cooled to room temperature, and 1N hydrochloric acid (4 ml) was added dropwise thereto in a water bath to quench the reaction. The mixture was extracted with chloroform (23 ml), and washed once with 1N hydrochloric acid (7.5 ml) and 4 times with pure water (7.5 ml). The solvent of the organic layer was evaporated, and the residue was precipitated with methanol (10 ml) to give 2-docosyloxy-9-fluorenone (934 mg, 1.85 mmol, 96%).

$^1$H-NMR(400 MHz)

0.88 (3H, t, J=7.0, $C_{21}H_{42}$-Me) 1.20-1.40 (36H, br, alkyl-H) 1.45 (2H, br, —O—$C_2H_4$=$CH_2$—$C_{19}H_{39}$) 1.79 (2H, m, —O—$CH_2$—$CH_2$—) 4.00 (2H, t, J=6.6, —O—$CH_2$—) 6.97 (1H, fluorenone C3-H) 7.19 (2H, fluorenone C1,7-H) 7.38-7.43 (3H, fluorenone C4,5,6-H) 7.59 (1H, fluorenone C8-H)

MS
505 [M+H]

1-2: Synthesis of
2-docosyloxy-9-(4-chlorophenyl)-9-fluorenol

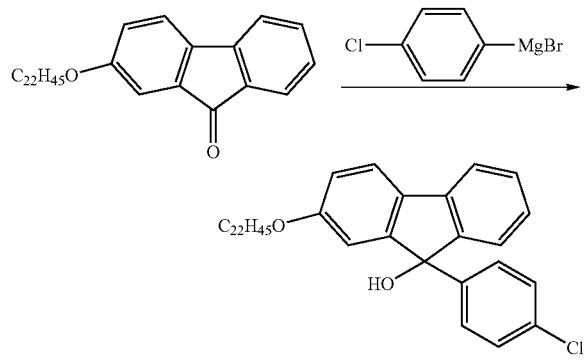

Under a nitrogen atmosphere, 2-docosyloxy-9-fluorenone (250 mg, 0.50 mmol) prepared in the above-mentioned 1-1 was suspended in THF (2.5 ml), and dissolved at 50° C. 4-Chlorophenylmagnesium bromide solution was added dropwise, and the mixture was stirred. After completion of the reaction, the reaction mixture was cooled to room temperature, 1N hydrochloric acid was added dropwise thereto in a water bath until foaming stopped to quench the reaction. The mixture was extracted with chloroform (15 ml), and washed 3 times with 1N hydrochloric acid (5 ml), 3 times with 5% NaHCO$_3$ solution (5 ml), and once with 20% NaCl solution (5 ml). The organic layer was dried over Na$_2$SO$_4$, and the solvent of the filtrate was evaporated. The obtained residue was isolated and purified by silica gel column chromatography, and precipitated with methanol (3 ml) to give 2-docosyloxy-9-(4-chlorophenyl)-9-fluorenol (270 mg, 0.44 mmol, 88%).

$^1$H-NMR(400 MHz)

0.88 (3H, t, J=7.0, $C_{21}H_{42}$-Me) 1.20-1.40 (36H, br, alkyl-H) 1.45 (2H, br, —O—$C_2H_4$=$CH_2$—$C_{19}H_{39}$) 1.75 (2H, m, —O—$CH_2$—$CH_2$—) 2.39 (1H, s, OH) 3.91 (2H, —O—$CH_2$—) 6.82 (1H, fluorene C3-H) 6.89 (1H, fluorene C1-H) 7.18 (1H, fluorene C7-H) 7.21-7.35 (6H, Ph-H, fluorenone-H) 7.56 (2H, fluorenone-H)

MS
599 [M-OH]

1-3: Synthesis of
2-docosyloxy-9-(4-chlorophenyl)-9-bromofluorene

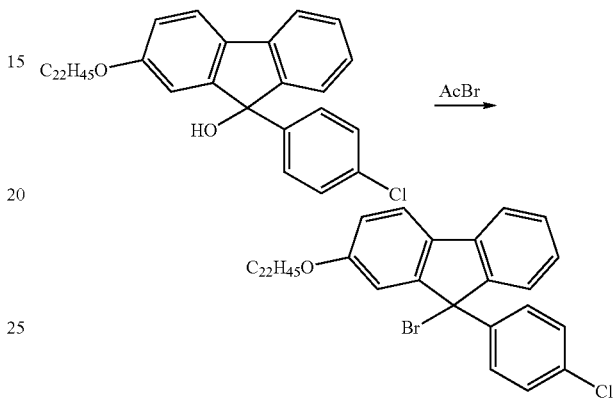

2-Docosyloxy-9-(4-chlorophenyl)-9-fluorenol (200 mg, 0.33 mmol) prepared in the above-mentioned 1-2 was dissolved in chloroform (2 ml), acetyl bromide (48 μl, 0.65 mmol) was added dropwise and the mixture was stirred for 1 hour. After completion of the reaction, the solvent was evaporated, and the residue was precipitated with acetonitrile (2 ml) to give 2-docosyloxy-9-(4-chlorophenyl)-9-bromofluorene (209 mg, 0.31 mmol, 95%).

$^1$H-NMR(400 MHz)

0.88 (3H, t, J=7.0, $C_{21}H_{42}$-Me) 1.20-1.40 (36H, br, alkyl-H) 1.44 (2H, br, —O—$C_2H_4$=$CH_2$—$C_{19}H_{39}$) 1.77 (2H, m, —O—$CH_2$—$CH_2$—) 3.95 (2H, —O—$CH_2$—) 6.92 (1H, fluorene-H) 6.98 (1H, fluorene-H) 7.21-7.26 (3H) 7.34 (1H) 7.43 (1H) 7.46-7.49 (2H) 7.55-7.59 (2H)

Example 2

2-1: Synthesis of 2,7-didocosyloxy-9-fluorenone

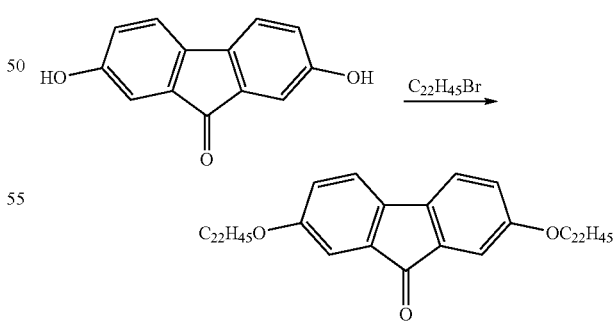

2,7-Dihydroxy-9-fluorenone (1 g, 4.71 mmol) was dissolved in DMF (40 ml), and potassium carbonate (1.95 g, 14.1 mmol) and docosyl bromide (96%, 4.02 g, 9.91 mmol) were added. The mixture was stirred overnight at 80° C., docosyl bromide (0.40 g, 0.99 mmol) was further added and the mixture was stirred overnight. After completion of the reaction, the reaction mixture was cooled to room temperature, 1N hydrochloric acid (120 ml) was added thereto in a water bath to allow precipitation. The crystals were collected by filtration and slurry washed once with 1N hydrochloric acid (40 ml), once with pure water (40 ml) and once with methanol (40 ml) to give 2,7-didocosyloxy-9-fluorenone (4.20 g, docosyl bromide mixture).

$^1$H-NMR(300 MHz)

0.88 (6H, t, J=6.6, $C_{21}H_{42}$-Me) 1.15-1.60 (80H, br, alkyl-H) 1.78 (4H, m, —O—C$\underline{H}_2$—C$\underline{H}_2$—) 3.98 (4H, t, J=6.6, —O—C$\underline{H}_2$—) 6.92 (2H, fluorenone C3,6-H) 7.14 (2H, d, J=2.1, fluorenone C1,8-H) 7.26 (2H, d, J=7.8, fluorenone C4,5-H) 7.59 (1H, fluorenone C8-H)

MS

829 [M+H]

2-2: Synthesis of 2,7-didocosyloxy-9-(4-chlorophenyl)-9-bromofluorene

In the same manner as in Example 1, 1-2, then 1-3 except that 2,7-didocosyloxy-9-fluorenone prepared in the above-mentioned 2-1 was used instead of 2-docosyloxy-9-fluorenone, 2,7-didocosyloxy-9-(4-chlorophenyl)-9-bromofluorene was obtained.

δ=0.88 (6H, t, O$C_{22}H_{45}$ C22-H) 1.1-1.6 (76H, br, O$C_{22}H_{45}$ C3-21-H) 1.75 (4H, m, O$C_{22}\underline{H}_{45}$ C2-H) 3.92 (4H, m, O$C_{22}\underline{H}_{45}$ C1-H) 6.87 (2H,m, fl C3,6-H) 6.94 (2H, d, fl C1,8-H) 7.20-7.40 (2H, m, Ph C2,6-$\underline{H}$) 7.42-7.49 (4H, m, Ph C3,5-$\underline{H}$, fl C4,5-H)

Example 3

3-1: Synthesis of 12-docosyloxy-dodecyl bromide

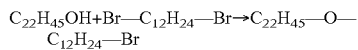

Sodium hydride (60%, 0.98 g, 24.5 mmol) washed with hexane was suspended in toluene (16 ml), 1-docosanol (4.00 g, 12.2 mmol) was added, 1,12-dibromododecane (8.04 g, 24.5 mmol) was added, and the mixture was stirred at 85° C. for 2 days. The reaction mixture was cooled to room temperature, 1N hydrochloric acid (30 ml) was added dropwise thereto in a water bath to quench the reaction. The mixture was extracted with chloroform (100 ml), and washed 3 times with 1N hydrochloric acid (30 ml), 3 times with 5% aqueous sodium hydrogen carbonate solution (30 ml), and once with 20% aqueous sodium chloride solution (30 ml). The organic layer was dried over sodium sulfate, and the solvent of the filtrate was evaporated. The residue was isolated and purified by silica gel column chromatography and precipitated with methanol (70 ml) to give 12-docosyloxy-dodecyl bromide (yield 78%).

$^1$H-NMR(300 MHz)

0.88 (3H, t, J=6.9, $C_{21}H_{42}$-Me) 1.10-1.65 (76H, br, alkyl-H) 1.85 (2H, m, —CH$_2$—C$\underline{H}_2$—Br) 3.39 (6H, m, $C_{21}H_{43}$—C$\underline{H}_2$—O—CH$_2$—$C_{10}\underline{H}_{20}$—C$\underline{H}_2$—Br)

MS

573[M+H], 575[M+H+2]

3-2: Synthesis of 2-(12-docosyloxy-dodecanoxy)-9-fluorenone

In the same manner as in Example 1, 1-1 except that 12-docosyloxy-dodecyl bromide prepared in the above-mentioned 3-1 was used instead of docosyl bromide, 2-(12-docosyloxy-dodecanoxy)-9-fluorenone was obtained.

δ=0.88 (3H, t, O$C_{22}H_{45}$ C22-H) 1.1-1.6 (58H, br, Alkyl-H) 1.77 (2H, m, fl-OCH$_2$C$\underline{H}_2$—) 3.39 (4H, t, —C$\underline{H}_2$OC$\underline{H}_2$—) 4.00 (2H, t, fl-OC$\underline{H}_2$—) 6.97 (1H, m, fl C3-H) 7.18 (2$\underline{H}$, m, fl C1,7-$\underline{H}$) 7.37-7.45 (3H, m, fl C4,5,6-$\underline{H}$) 7.60 (1H, d, fl C8-$\underline{H}$)

3-3: Synthesis of 2-(12-docosyloxy-dodecanoxy)-9-(3-fluorophenyl)-9-bromofluorene In the same manner as in Example 1, 1-2, then 1-3 except that 2-(12-docosyloxy-dodecanoxy)-9-fluorenone prepared in the above-mentioned 3-2 was used instead of 2-docosyloxy-9-fluorenone and 3-fluorophenylmagnesium bromide instead of 4-chlorophenylmagnesium bromide, 2-(12-docosyloxy-dodecanoxy)-9-(3-fluorophenyl)-9-bromofluorene was obtained.

δ=0.88 (3H, t, O$C_{22}H_{45}$ C22-H) 1.2-1.6 (58H, br, Alkyl-H) 1.77 (2H, m, fl-OCH$_2$C$\underline{H}_2$—) 3.38 (4H, t, —C$\underline{H}_2$OC$\underline{H}_2$—) 3.95 (2H, m, fl-OC$\underline{H}_2$—) 6.91 (1H, m, fl C3-H) 6.94 (1$\underline{H}$, m, fl C1-H) 7.00 (1H, d, Ph C6-H) 7.20-7.38 (5$\underline{H}$, m, Ph C2,4,5-$\underline{H}$, fl C6,7-$\underline{H}$) 7.44 (1H, d, fl C8-$\underline{H}$) 7.58 (2H, d, fl C4,5-$\underline{H}$)

Example 4

4-1: Synthesis of 1,12-bis-(12-bromododecyloxy)-dodecane

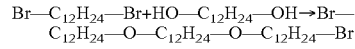

Sodium hydride (60%, 652 mg, 16.3 mmol) washed with hexane was suspended in toluene (3 ml), 1,12-dodecanediol (1.50 g, 7.41 mmol) was added, 1,12-dibromododecane (6.08 g, 18.5 mmol) was added, and the mixture was stirred at 80° C. for 4 days. The reaction mixture was cooled to room temperature, and pure water (30 ml) was added dropwise thereto in a water bath to quench the reaction. The mixture was extracted with chloroform (100 ml), and washed 3 times with 1N hydrochloric acid (30 ml), 3 times with 5% aqueous sodium hydrogen carbonate solution (30 ml), and once with 20% aqueous sodium chloride solution (30 ml). The organic layer was dried over sodium sulfate and the solvent of the filtrate was evaporated. The residue was isolated and purified by silica gel column chromatography, and precipitated with methanol (50 ml) to give 1,12-bis-(12-bromododecyloxy)-dodecane (yield 56%).

$^1$H-NMR(300 MHz)

1.20-1.65 (56H, br, alkyl-H) 1.85 (4H, dt, —C$\underline{H}_2$—CH$_2$—Br) 3.39 (12H, m, —O—C$\underline{H}_2$, —C$\underline{H}_2$—Br)

4-2: Synthesis of 1,12-bis-[12-(2'-O-9-fluorenone)-dodecyloxy]-dodecane

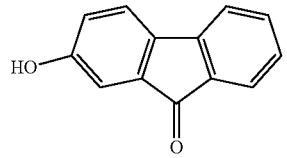
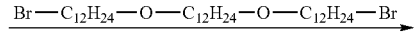

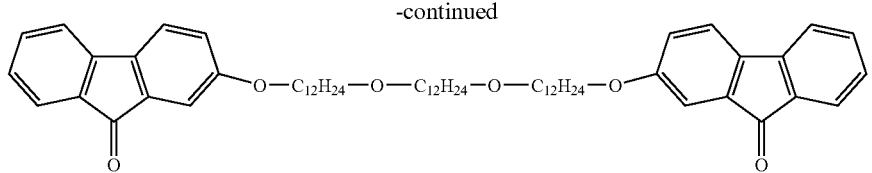

2-Hydroxy-9-fluorenone (577 mg, 2.94 mmol) was dissolved in DMF (10 ml), and potassium carbonate (595 mg, 4.37 mmol) and 1,12-bis-(12-bromododecyloxy)-dodecane (1 g, 1.44 mmol) prepared in the above-mentioned 4-1 were added. The mixture was stirred at 80° C. overnight, 2-hydroxy-9-fluorenone (56 mg, 0.29 mmol) was added, and the mixture was stirred overnight. After completion of the reaction, the reaction mixture was cooled to room temperature, and 1N hydrochloric acid (15 ml) was added dropwise thereto in a water bath to quench the reaction. The mixture was extracted with chloroform (50 ml), and washed 3 times with 1N hydrochloric acid (15 ml), 3 times with 5% aqueous sodium hydrogen carbonate solution (30 ml) and once with 20% aqueous sodium chloride solution (30 ml). The organic layer was dried over sodium sulfate, the solvent of the filtrate was evaporated, and the residue was precipitated with methanol (20 ml) to give 1,12-bis-[12-(2'-O-9-fluorenone)-dodecyloxy]-dodecane (1.28 g, 96%).

$^1$H-NMR(300 MHz)

1.20-1.65 (56H, br, alkyl-H) 1.79 (4H, m, fluorenone-O—CH$_2$—CH$_2$—) 3.38 (8H, t, J=6.6, —C$_{11}$H$_{22}$—CH$_2$—O—CH$_2$—C$_{11}$H$_{22}$—) 4.00 (4H, t, J=6.6, fluorenone-O—CH$_2$—) 6.97 (2H, dd, J=2.4, 8.1, fluorenone C3-H) 7.19 (4H, dt, J=1.8,6.9 fluorenone C1,7-H) 7.40 (6H, m, fluorenone C4,5,6-H) 7.59 (1H, d, J=7.2, fluorenone C8-H)

4-3: Synthesis of 1,12-bis-[12-(2'-O-9-(4-chlorophenyl)-9-fluorenol)-dodecyloxy]-dodecane

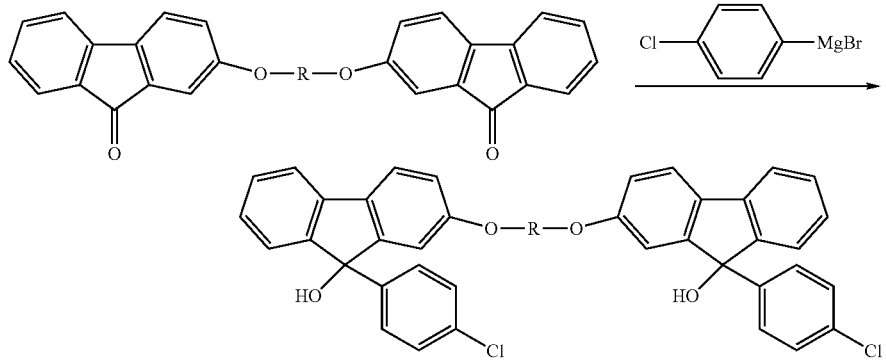

wherein —R— is —C$_{12}$H$_{24}$OC$_{12}$H$_{24}$OC$_{12}$H$_{24}$—.

Under a nitrogen atmosphere, 1,12-bis-[12-(2'-O-9-fluorenone)-dodecyloxy]-dodecane (350 mg, 0.38 mmol) was suspended in THF (3.5 ml) and dissolved at 50° C. 4-Chlorophenylmagnesium bromide solution (5.65 ml, 5.65 mmol) was added dropwise thereto, and the mixture was stirred for 2 hours. After completion of the reaction, the reaction mixture was cooled to room temperature, and 1N hydrochloric acid was added dropwise thereto in a water bath until foaming stopped to quench the reaction. The mixture was extracted with chloroform (15 ml), and washed 3 times with 1N hydrochloric acid (5 ml), 3 times with 5% NaHCO$_3$ solution (5 ml) and once with 20% NaCl solution (5 ml). The organic layer was dried over Na$_2$SO$_4$, and the solvent of the filtrate was evaporated. The obtained residue was purified by silica gel column chromatography to give 1,12-bis-[12-(2'-O-9-(4-chlorophenyl)-9-fluorenol)-dodecyloxy]-dodecane (214 mg, 0.19 mmol, 49%). δ=1.2-1.6 (56H, br, Alkyl-H) 1.73 (4H, q, fl-OCH$_2$CH$_2$—) 2.54 (2H, s, —OH) 3.36 (8H, t, —CH$_2$OCH$_2$—) 3.90 (4H, t, fl-OCH$_2$—) 6.82 (2H, s, fl C1-H) 6.89 (2H, d, fl C3-H) 7.15-7.45 (14H, m, fl C6,7,8-H, Ph C2,3,5,6-H,) 7.54 (4H, d, fl C4,5-H)

4-4: Synthesis of 1,12-bis-[12-(2'-O-9-(4-chlorophenyl)-9-bromofluorene)-dodecyloxy]-dodecane

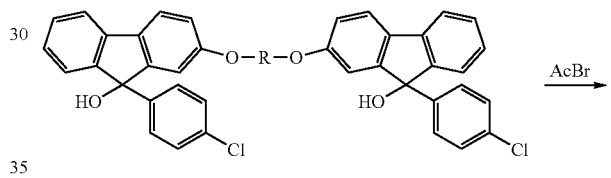

-continued

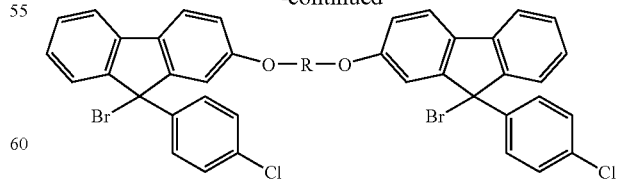

wherein —R— is —C$_{12}$H$_{24}$OC$_{12}$H$_{24}$OC$_{12}$H$_{24}$—.

1,12-bis-[12-(2'-O-9-(4-Chlorophenyl)-9-fluorenol)-dodecyloxy]-dodecane (214 mg, 0.19 mmol) was dissolved in chloroform (2 ml), acetyl bromide (69 μl, 0.93 mmol) was added dropwise thereto, and the mixture was stirred for 3 hours. After completion of the reaction, the solvent was evaporated, and the residue was decanted with acetonitrile (2 ml) to give 1,12-bis-[12-(2'-O-9-(4-chlorophenyl)-9-bromofluorene)-dodecyloxy]-dodecane (200 mg, 0.16 mmol, 84%).

δ=1.2-1.6 (56H, br, Alkyl-H) 1.73 (4H, Br, fl-OCH$_2$CH$_2$—) 3.38 (8H, t, —CH$_2$OCH$_2$—) 3.88 (4H, m, fl-OCH$_2$—) 6.92 (2H, d, fl C3-H) 6.98 (2H, s, fl C1-H) 7.19-7.27 (6H, m, fl C7-H, Ph C2,6-H,) 7.34 (2H, t, fl C6-H) 7.43 (2H, d, fl C8-H) 7.48 (4H, d, Ph C3,5-H) 7.55 (4H, d, fl C4,5-H)

4-5: Synthesis of Z-alanine-fluorene Anchor Compound

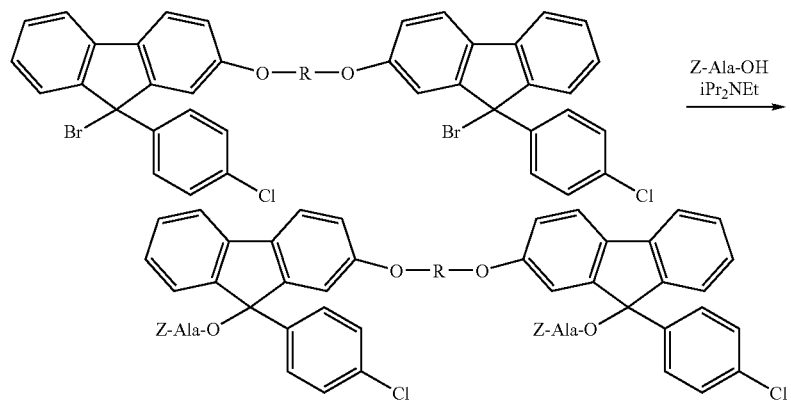

wherein —R— is —C$_{12}$H$_{24}$OC$_{12}$H$_{24}$OC$_{12}$H$_{24}$—.

1,12-bis-[12-(2'-O-9-(4-Chlorophenyl)-9-bromofluorene)-dodecyloxy]-dodecane (200 mg, 0.16 mmol) was dissolved in chloroform (2 ml), Z-alanine (210 mg, 0.94 mmol) was added and N-ethyldiisopropylamine (216 μl, 1.25 mmol) was added, and the mixture was stirred at 50° C. overnight. After completion of the reaction, the solvent was dissolved in chloroform (4 ml), and the mixture was washed once with pure water (2 ml), 5 times with 10% aqueous sodium carbonate solution (2 ml), twice with pure water (2 ml) and once with 20% aqueous sodium chloride solution (2 ml), dried over sodium sulfate, and the solvent was evaporated to give Z-alanine-fluorene anchor compound (221 mg, 0.14 mmol, 90%).

δ=1.2-1.6 (59H, br, Ala CH$_3$, Alkyl-H) 1.76 (4H, q, fl-OCH$_2$CH$_2$—) 3.38 (8H, t, —CH$_2$OCH$_2$—) 3.94 (4H, m, fl-OCH$_2$—) 4.50 (2H, Br, Ala α-H) 5.07 (4H, s, Z Ph-CH$_2$O—) 5.16 (2H, Br, NH) 6.77 (2H, d, fl C3-H) 6.88 (2H, d, fl C1-H) 7.15-7.45 (16H, m, fl C6,7,8-H, Z Ph-H) 7.59 (4H, d, fl C4,5-H)

Example 5

5-1: Synthesis of trioctadecanoxypentaerythritol

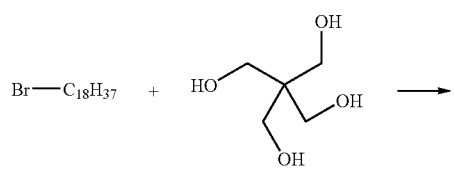

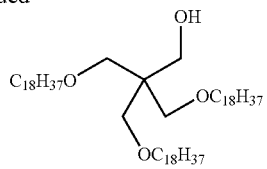

To pentaerythritol (1.5 g, 11.0 mmol) were added DMF (100 ml), 1-bromooctadecane (11.4 g, 34.2 mmol) and NaH (60 wt %, 1.54 g, 38.5 mmol), and the mixture was stirred at 100° C. for 22 hours. The reaction mixture was cooled to room temperature, chloroform (150 ml) was added, 1N hydrochloric acid (150 ml) was further added dropwise thereto. After stirring for a while, the aqueous layer was discarded, and the organic layer was further washed with 1N hydrochloric acid (100 ml) and water (100 ml). The organic layer was evaporated under reduced pressure, the residue was precipitated with methanol (150 ml), and the obtained crystals were slurry washed with methanol (150 ml). Crude crystals were dried and purified by silica gel column chromatography (hexane:chloroform=1:1→hexane:ethyl acetate=10:1) to give trioctadecanoxypentaerythritol (2.21 g, 2.47 mmol, yield 23%).

$^1$H-NMR (300 MHz)
0.88 (3H, t, J=6.9, —OC$_{17}$H$_{34}$-Me) 1.10-1.65 (96H, br, C18Alkyl-H) 3.12 (1H, t, J=6.0, OH) 3.38 (6H, t, J=6.3, —C—(CH$_2$—O—CH$_2$—C$_{17}$H$_{35}$)$_3$) 3.43 (6H, s, —C—(CH$_2$O—C$_{18}$H$_{37}$)$_3$) 3.70 (2H, d, J=5,7, HO—CH$_2$—)

5-2: Synthesis of 1-(3-iodo-2,2-bis-octadecanoxymethyl-propoxy)octadecane

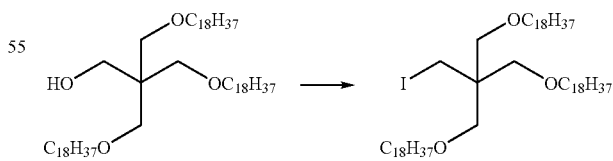

Trioctadecanoxypentaerythritol (500 mg, 560 μmol) prepared in the above-mentioned 5-1 was dissolved in toluene (10 ml), triphenylphosphine (294 mg, 1.12 mmol), imidazole (76.2 mg, 1.12 mmol) and iodine (284 mg, 1.12 mmol) were added, and the mixture was stirred at 100° C. overnight. The reaction mixture was cooled to room temperature, toluene (10 ml) was added, and the mixture was washed with water (5 ml×3). The organic layer was separated and evaporated under reduced pressure, and the residue was precipitated with acetonitrile (10 ml) to give 1-(3-iodo-2,2-bis-octadecanoxymethyl-propoxy)octadecane (555 mg, 553 μmol, yield 98%).

$^1$H-NMR (300 MHz)

0.88 (3H, t, J=6.9, —OC$_{17}$H$_{34}$-Me) 1.10-1.65 (96H, br, C18Alkyl-H) 3.33 (6H, s, —C—(C$\underline{H_2}$—O—C$_{18}$H$_{37}$)$_3$) 3.38 (6H, t, J=6.3, —C—(CH$_2$—O—C$\underline{H_2}$C$_{17}$H$_{35}$)$_3$) 3.48 (2H, s, I—C$\underline{H_2}$—)

5-3: Synthesis of 2-(3-octadecyloxy-2,2-bis-octadecyloxymethyl-propoxy)-fluorenone

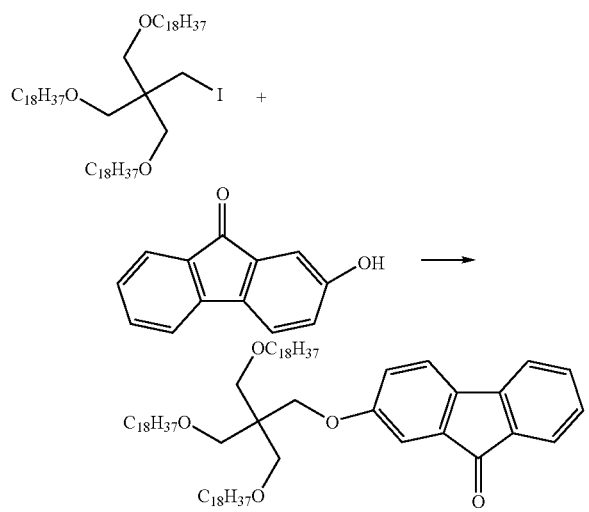

1-(3-Iodo-2,2-bis-octadecanoxymethyl-propoxy)octadecane (500 mg, 102 μmol) and 2-hydroxy-9-fluorenone (30 mg, 152 μmol) were dissolved in DMF (2 ml), potassium carbonate (21 mg, 152 μmol) was added, and the mixture was stirred at 130° C. After completion of the reaction, 0.5N hydrochloric acid (6 ml) was added, the precipitate was filtered, and the precipitate was washed with acetonitrile and water to give 2-(3-octadecyloxy-2,2-bis-octadecyloxymethyl-propoxy)-9-fluorenone (101 mg, 94 μmol).

5-4: Synthesis of 2-(3-octadecyloxy-2,2-bis-octadecyloxymethyl-propoxy)-9-(4-chlorophenyl)-9-fluorenol

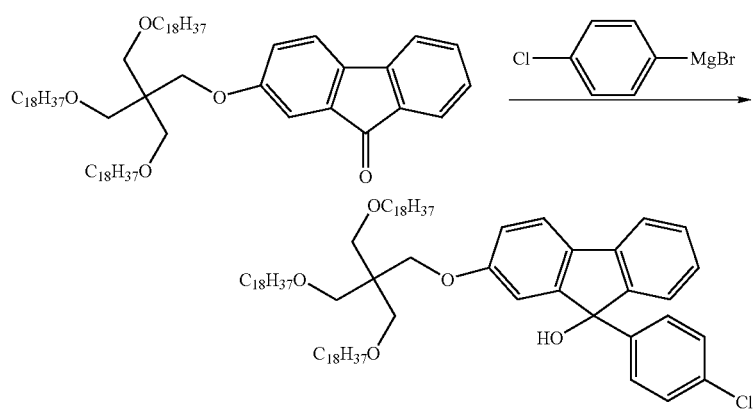

Under a nitrogen atmosphere, 2-(3-octadecyloxy-2,2-bis-octadecyloxymethyl-propoxy)-9-fluorenone (75 mg, 73 μmol) was suspended in THF (1 ml) to allow dissolution at 50° C. 4-Chlorophenylmagnesium bromide solution (0.15 ml, 0.15 mmol) was added dropwise, and the mixture was stirred for 30 minutes. After completion of the reaction, the reaction mixture was cooled to room temperature, extracted with chloroform (3 ml), and washed 3 times with 1N hydrochloric acid (1 ml), 3 times with 5% NaHCO$_3$ solution (1 ml) and once with 20% NaCl solution (1 ml). The organic layer was dried over Na$_2$SO$_4$, the solvent of the filtrate was evaporated, and the obtained residue was separated and purified by silica gel column chromatography and crystallized from methanol (1 ml) to give 2-(3-octadecyloxy-2,2-bis-octadecyloxymethyl-propoxy)-9-(4-chlorophenyl)-9-fluorenol (66 mg, 56μ mmol, 77%).

δ=0.88 (9H, t, J=6.9 Hz, OC$_{18}$H$_{37}$ C18-H) 1.1-1.6 (96H, br, OC$_{18}$H$_{37}$ C2-17-H) 2.36 (1H, s, —OH) 3.$\overline{35}$ (6H, t, OC$_{18}$H$_{37}$ C1-H) 3.45 (6H, $\overline{s}$, —CH$_2$—OC$_{18}$H$\overline{37}$) 3.92 (2H, m, fl-OCH$_2$—) 6.84 (1H, s, fl C1-$\overline{H}$) 6.91 (1H, d, fl C3-H) 7.13-7.35 ($\overline{7H}$, m, Ph C2,3,5,6-H, fl $\overline{C}$6,7,8-H) 7.54 (2H, $\overline{m}$, fl C4,5-H)

5-5: Synthesis of 2-(3-octadecyloxy-2,2-bis-octadecyloxymethyl-propoxy)-9-(4-chlorophenyl)-9-bromofluorene

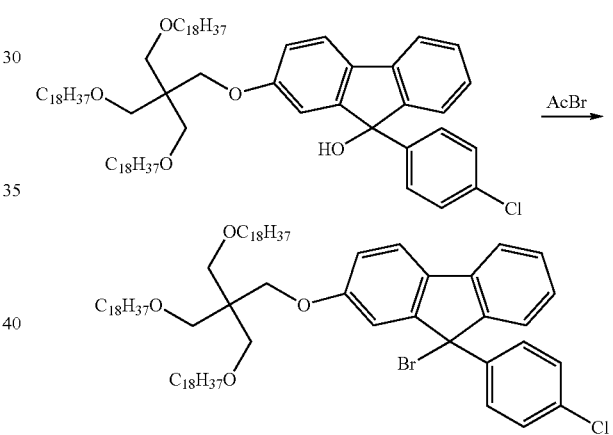

2-(3-Octadecyloxy-2,2-bis-octadecyloxymethyl-propoxy)-9-(4-chlorophenyl)-9-fluorenol (66 mg, 56 μmol) was dissolved in chloroform (1 ml), acetyl bromide (41 μl, 0.55 mmol) was added dropwise thereto and the mixture was stirred for 2 hours. After completion of the reaction, the solvent was evaporated, and the residue was crystallized from acetonitrile (1 ml) to give 2-(3-octadecyloxy-2,2-bis-octadecyloxymethyl-propoxy)-9-(4-chlorophenyl)-9-bromofluorene (55 mg, 44 μmol, 79%). δ=0.88 (9H, t, J=6.9 Hz, $OC_{18}H_{37}$ C18-$\underline{H}$) 1.1-1.6 (96H, br, $OC_{18}H_{37}$ C2-17-$\underline{H}$) 3.37 (6H, t, $OC_{18}\overline{H_{37}}$C1-$\underline{H}$) 3.47 (6H, s, —$\underline{CH_2}$—$OC_{18}\overline{H_{37}}$) 3.97 (2H, m, fl-$OC\underline{H_2}$—) $\overline{6.93}$ (1H, d, fl C3-$\underline{H}$) 6.95 (1H, s, fl C1-$\underline{H}$) 7.13-7.57 ($\overline{9H}$, m, Ph C2,3,5,6-$\underline{H}$, fl $\overline{C}$4,5,6,7,8-$\underline{H}$)

Example 6

Introduction of Z-Ala into Fluorene Anchor Compound

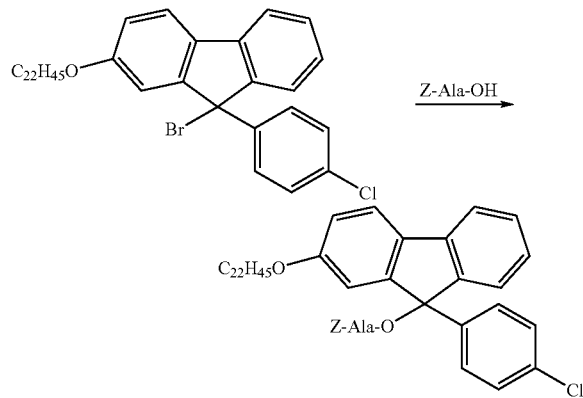

2-Docosyloxy-9-(4-chlorophenyl)-9-bromofluorene (200 mg, 0.29 mmol) obtained in Example 1 was dissolved in chloroform (2 ml), Z-alanine (197 mg, 0.88 mmol) was added and N-ethyldiisopropylamine (202 μl, 1.17 mmol) was added, and the mixture was stirred at 50° C. overnight. After completion of the reaction, the solvent was evaporated, and the residue was precipitated with acetonitrile (2 ml) to give Z-alanine-fluorene anchor compound (178 mg, 0.22 mmol, 74%).
$^1$H-NMR(400 MHz)
0.88 (3H, t, J=7.0, $C_{21}H_{42}$-$\underline{Me}$) 1.20-1.40 (39H, br, alkyl-$\underline{H}$, Alanine $\underline{Me}$) 1.45 (2H, br, —O—$C_2H_4$—$\underline{CH_2}$—$C_{19}H_{39}$) $\overline{1.73}$ (2H, br, —O—$CH_2$—$\underline{CH_2}$—) 3.89 (2H, —$\overline{O}$—$\underline{CH_2}$—) 4.51 (1H, br, Z—NH—$\underline{CH}$) $\overline{5.07}$ (2H, s, benzyl-$\underline{H}$) 5.19 $\overline{(1H}$, br, s, Z—$N\underline{H}$—) 6.78 (1$\underline{H}$, d, J=13.5, fluorene-$\underline{H}$) 6.90 (1H, d, J=6.3, fluor$\overline{ene}$-$\underline{H}$) 7.14-7.37 (12H) 7.57-7.60 (2H)

Example 7

Introduction of Fmoc-Ala-OH into Fluorene Anchor Compound

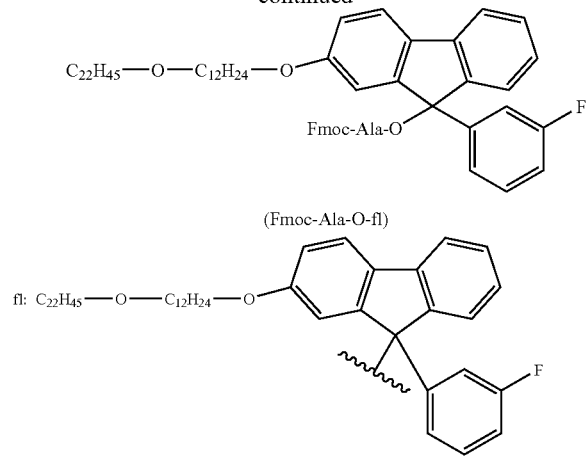

The fluorene anchor prepared in Example 3; 2-(12-docosyloxy-dodecanoxy)-9-(3-fluorophenyl)-9-bromofluorene (600 mg, 0.71 mmol) was dissolved in chloroform (6 ml), Fmoc-Ala-OH.H$_2$O (699 mg, 2.12 mmol) and diisopropylethylamine (366 μl, 2.12 mmol) were added, and the mixture was stirred at 70° C. overnight. After completion of the reaction, the solvent was evaporated, the residue was precipitated with acetonitrile (6 ml) to give Fmoc-Ala-O-fl (726 mg, 0.67 mmol, 95%).
$^1$H-NMR (300 MHz)
0.88 (3H, t, J=6.9, —$OC_{17}H_{34}$-$\underline{Me}$) 1.20-1.65 (63H, br, Alkyl-$\underline{H}$, Ala $\underline{Me}$) 1.71 (2H, br, fl-$\overline{O}$—$CH_2$—$\underline{CH_2}$—) 3.38 (4H, t, $\overline{J}$=6.6, —$\underline{CH_2}$—O—$\underline{CH_2}$—$C_{21}H_{43}$) 3.89 $\overline{(2H}$, br, fl-O—$\underline{CH_2}$—) 4.16 ($\overline{1H}$, t, J=6.9, fluorene (Fmoc) C9-$\underline{H}$) 4.34 (2H, d, J=6.3, fluorene (Fmoc)-$\underline{CH_2}$—O) 4.53 (1H, br, Ala α-$\underline{H}$) 5.25 (1H, br, Fmoc-N$\underline{H}$) 6.80 $\overline{(1H}$, br, m, fluorene-$\underline{H}$ or Ph-$\underline{H}$) 6.85-7.05 (4H, br, m, fluorene-$\underline{H}$ or Ph-$\underline{H}$) 7.10-$\overline{7.30}$ (2$\underline{H}$, br, m, fluorene-$\underline{H}$ or Ph-$\underline{H}$) 7.37 ($\overline{3H}$, t, J=7.2, fluorene-$\underline{H}$ or Ph-$\underline{H}$) 7.52 (2$\underline{H}$, br, d, J=6.9, fluorene-$\underline{H}$ or Ph-$\underline{H}$) 7.60 $\overline{(2H}$, br, fluorene-$\underline{H}$ or Ph-$\underline{H}$) 7.73 (2H, d, J=7.2, fluorene-$\underline{H}$ or Ph-$\underline{H}$)
$\underline{MS}$
784 [M-(Fmoc-Ala)]

Example 8

Removal of Fmoc from Fmoc-Ala-O-fl

Fmoc-Ala-O-fl→H-Ala-O-fl

Fmoc-Ala-O-fl (700 mg, 0.65 mmol) prepared in Example 7 was dissolved in chloroform-acetonitrile (1:1, 7 ml), diethylamine (1.36 ml, 13.0 mmol) was added dropwise thereto at 0° C., and the mixture was stirred at room temperature for 2 hours. Diethylamine (1.36 ml, 13.0 mmol) was further added dropwise thereto, and the mixture was stirred for 1 hour. After completion of the reaction, the solvent was evaporated, and the residue was precipitated with acetonitrile (6 ml) to give H-Ala-O-fl (542 mg, 0.63 mmol, 97% (total yield 93% vs fl-Br)).
$^1$H-NMR (300 MHz)
0.88 (3H, t, J=6.9, —$OC_{17}H_{34}$-$\underline{Me}$) 1.20-1.65 (63H, br, Alkyl-$\underline{H}$, Ala $\underline{Me}$) 1.74 (2H, br, fl-O-$\underline{CH_2}$—$CH_2$—) 3.38 (4H, t, J=6.6, —$\underline{CH_2}$—O—$CH_2$—$C_{21}H_{43}$) 3.63 ($\overline{1H}$, br, Ala α-$\underline{H}$) 3.90 (2H, d, $\overline{J}$=6.6, fluor$\overline{ene}$-O—$\underline{CH_2}$—) 6.80 (1H, d, J=2.1, fluorene-$\underline{H}$ or Ph-$\underline{H}$) 6.85-7.07 (4$\underline{H}$, m, fluorene-$\underline{H}$ or Ph-$\underline{H}$)

7.10-7.30 (3H, m, fluorene-H or Ph-H) 7.35 (1H, t, J=7.4, fluorene-H or Ph-H) 7.60 (2H, m, fluorene-H or Ph-H)

MS

784 [M-(H-Ala-O)]

Example 9

Condensation of Fmoc-Pro-OH

H-Ala-O-fl (530 mg, 0.62 mmol) prepared in Example 8 was dissolved in chloroform (7 ml), HOBt (18 mg, 0.13 mmol) and Fmoc-Pro-OH (230 mg, 0.68 mmol) were added, EDC.HCl (144 mg, 0.75 mmol) was added at 0° C., and the mixture was stirred at room temperature overnight. After completion of the reaction, the solvent was evaporated, and the residue was precipitated with methanol (7 ml) to give Fmoc-Pro-Ala-O-fl (695 mg, 0.59 mmol, 95% (total yield 89% vs fl-Br)).

$^1$H-NMR (300 MHz)

0.88 (3H, t, J=6.9, —OC$_{17}$H$_{34}$-Me) 1.20-2.00 (67H, br, Alkyl-H, Pro N—CH$_2$—CH$_2$—CH$_2$—CH, Ala Me) 3.38 (4H, t, J=6.6, —CH$_2$—O—CH$_2$—C$_{21}$H$_{43}$) 3.48 (2H, t, Fmoc-N—CH$_2$—) 3.88 (2H, br, fl-O—CH$_2$—) 4.10-4.50 (4H, br, fluorene (Fmoc) C9-H, fluorene (Fmoc)-CH$_2$—O, Ala α-H) 4.68 (1H, br, Pro α-H) 6.70-7.60 (16H, br, m, fluorene-H or Ph-H) 7.75 (2H, d, J=7.2, fluorene-H or Ph-H)

Example 10

Removal of Fmoc from Fmoc-Pro-Ala-O-fl

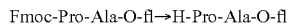

Fmoc-Pro-Ala-O-fl (660 mg, 0.56 mmol) prepared in Example 9 was dissolved in chloroform-acetonitrile (7:6, 6.5 ml), diethylamine (1.16 ml, 11.1 mmol) was added dropwise thereto at 0° C., and the mixture was stirred at room temperature for 2 hours. After completion of the reaction, the solvent was evaporated, and the residue was precipitated with acetonitrile (7 ml) to give H-Pro-Ala-O-fl (528 mg, 0.55 mmol, 98% (total yield 88% vs fl-Br)).

$^1$H-NMR (300 MHz)

0.88 (3H, t, J=6.9, —OC$_{17}$H$_{34}$-Me) 1.15-1.80 (67H, br, Alkyl-H, Pro HN—CH$_2$—CH$_2$—CH$_2$—CH, Ala Me) 1.87 (1H, m, Pro HN—CH$_2$—CH$_2$—CH$_2$—CH) 2.11 (1H, m, Pro HN—CH$_2$—CH$_2$—CH$_2$—CH) 2.88 (2H, m, Pro HN—CH$_2$) 3.38 (4H, t, J=6.6, —CH$_2$—O—CH$_2$—C$_{21}$H$_{43}$) 3.69 (1H, m, Pro α-H) 3.90 (2H, d, J=6.6, fluorene-O—CH$_2$—) 4.72 (1H, m, Ala α-H) 6.79 (1H, m, fluorene-H or Ph-H) 6.85-6.95 (2H, m, fluorene-H or Ph-H) 7.01 (2H, d, J=8.1, fluorene-H or Ph-H) 7.10-7.30 (2H, m, fluorene-H or Ph-H) 7.34 (1H, m, fluorene-H or Ph-H) 7.59 (2H, m, fluorene-H or Ph-H) 7.96 (1H, br, d, J=7.2, fluorene-H or Ph-H)

Example 11

Condensation of Fmoc-Ile-OH

H-Pro-Ala-O-fl (510 mg, 0.54 mmol) prepared in Example 10 was dissolved in chloroform (7 ml), HOBt (15 mg, 0.11 mmol) and Fmoc-Ile-OH (206 mg, 0.58 mmol) were added, EDC.HCl (123 mg, 0.64 mmol) was added at 0° C., and the mixture was stirred at room temperature overnight. After completion of the reaction, the solvent was evaporated, and the residue was precipitated with methanol (7 ml) to give Fmoc-Ile-Pro-Ala-O-fl (642 mg, 0.50 mmol, 93% (total yield 82% vs fl-Br)).

$^1$H-NMR (300 MHz)

0.88 (3H, t, J=6.9, —OC$_{17}$H$_{34}$-Me) 1.20-2.20 (75H, br, m, Alkyl-H, Ile Me-CH$_2$—CH-Me, Pro N—CH$_2$CH$_2$—CH$_2$—CH, Ala Me) 2.30 (1H, br, s, Ile Me-CH$_2$—CH-Me) 3.38 (4H, t, J=6.6, —CH$_2$—O—CH$_2$—C$_{21}$H$_{43}$) 3.58 (1H, br, Pro CO—N—CH$_2$—) 3.70 (1H, br, Pro CO—N—CH$_2$—) 3.88 (2H, br, t, J=6.6, fl-O—CH$_2$—) 4.19 (1H, t, J=6.6, fluorene (Fmoc) C9-H) 4.25-4.45 (3H, m, fluorene (Fmoc)-CH$_2$—O, Ile or Pro or Ala α-H) 4.50 (1H, br, m, Ile or Pro or Ala α-H) 4.66 (1H, br, m, Ile or Pro or Ala α-H) 5.40 (1H, d, J=9.3, Fmoc-NH—) 6.75-7.45 (12H, m, fluorene-H or Ph-H) 7.57 (4H, br, fluorene-H or Ph-H) 7.75 (2H, d, J=7.8, fluorene-H or Ph-H)

Example 12

Removal of Fmoc from Fmoc-Ile-Pro-Ala-O-fl

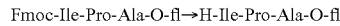

Fmoc-Ile-Pro-Ala-O-fl (620 mg, 0.48 mmol) prepared in Example 11 was dissolved in chloroform-acetonitrile (7:6, 6.5 ml), diethylamine (1.00 ml, 9.57 mmol) was added dropwise thereto at 0° C., and the mixture was stirred at room temperature for 1 hour. Diethylamine (1.00 ml, 9.57 mmol) was added dropwise thereto, and the mixture was stirred for 2 hours. After completion of the reaction, the solvent was evaporated, and the residue was precipitated with acetonitrile (6 ml) to give H-Ile-Pro-Ala-O-fl (500 mg, 0.47 mmol, 98% (total yield 80% vs fl-Br)).

$^1$H-NMR (300 MHz)

0.90 (9H, m, —OC$_{17}$H$_{34}$-Me, Ile Me) 1.20-2.20 (75H, br, m, Alkyl-H, Ile Me-CH$_2$—CH-Me, Pro N—CH$_2$—CH$_2$—CH$_2$—CH, Ala Me) 2.35 (1H, br, s, Ile Me-CH$_2$—CH-Me) 3.38 (5H, m, —CH$_2$—O—CH$_2$—C$_{21}$H$_{43}$, Ile α-H) 3.52 (2H, dd, J=6.0, 7.8, Pro N—CH$_2$) 3.90 (2H, t, J=6.6, fluorene-O—CH$_2$—) 4.50-4.70 (2H, m, Pro, Ala α-H) 6.82 (1H, m, fluorene-H or Ph-H) 6.91 (2H, m, fluorene-H or Ph-H) 7.01 (2H, m, fluorene-H or Ph-H) 7.10-7.40 (4H, m, fluorene-H or Ph-H) 7.58 (2H, m, fluorene-H or Ph-H)

Example 13

Condensation of Fmoc-Ser(tBu)-OH (SEQ ID NO: 1)

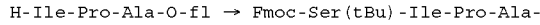

H-Ile-Pro-Ala-O-fl (490 mg, 0.46 mmol) prepared in Example 12 was dissolved in chloroform (6 ml), HOBt (13 mg, 0.10 mmol) and Fmoc-Ser(tBu)-OH (194 mg, 0.51 mmol) were added, EDC-HCl (107 mg, 0.56 mmol) was added at 0° C. and the mixture was stirred at room temperature overnight. After completion of the reaction, the solvent was evaporated, and the residue was precipitated with methanol (7 ml) to give Fmoc-Ser(tBu)-Ile-Pro-Ala-O-fl (SEQ ID NO: 1) (610 mg, 0.43 mmol, 94% (total yield 74% vs fl-Br)).

Example 14

Removal of Anchor from Fmoc-Ser(tBu)-Ile-Pro-Ala-O-fl (SEQ ID NO: 1)

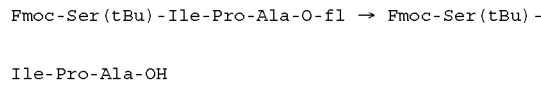

(SEQ ID NOS: 1 and 2, respectively, in order of appearance)

Fmoc-Ser(tBu)-Ile-Pro-Ala-O-fl (SEQ ID NO: 1) (600 mg, 0.42 mmol) prepared in Example 13 was dissolved in TFA-chloroform (1%, 6 ml, TFA: about 2 eq), and the mixture was stirred at room temperature. After 30 min, TFA (60 μl, about 2 eq) was added dropwise thereto, 1.5 hr later, TFA (180 μabout 6 eq) was added dropwise thereto and the mixture was stirred for 1.5 hr. After completion of the reaction, the solvent was evaporated, acetonitrile (6 ml) was added to the residue and the precipitate was filtered off. The filtrate was concentrated and washed with hexane (6 ml) to give Fmoc-Ser(tBu)-Ile-Pro-Ala-OH (SEQ ID NO: 2) (224 mg, 0.36 mmol, 86%).

MS

Fmoc-S(tBu)IPA-OH (SEQ ID NO: 2): 665 [M+H] Fmoc-S(H)IPA-OH (SEQ ID NO: 2): 609 [M+H]

Similarly, Fmoc-Ser(tBu)-Ile-Pro-Ala-O-fl (SEQ ID NO: 1) (100 mg, 0.07 mmol) prepared in Example 13 was dissolved in trifluoroethanol and chloroform and the mixture was stirred at 50° C. After completion of the reaction, the solvent was evaporated, methanol (3 ml) was added to the residue and the precipitate was filtered off. The filtrate was concentrated, and hexane (6 ml) was added. The precipitate was collected by filtration to give Fmoc-Ser(tBu)-Ile-Pro-Ala-OH (SEQ ID NO: 2) (30 mg).

Example 15

15-1: Synthesis of (3,4,5-tris(octadecyloxy)-cyclohexyl)-methanol

Methyl trioctadecyloxy-cyclohexylcarboxylate (2.87 g, 3.03 mmol) was dissolved in dehydrating THF (30 mL), DIBAL-H (9 mmol) was added and the mixture was stirred at room temperature for 30 minutes. 1N Hydrochloric acid (10 mL) was added, and THF was evaporated under reduced pressure. Chloroform (30 mL) and 1N hydrochloric acid (30 mL) were added to separate the layer. The organic layer was recovered and the solvent was evaporated. The residue was crystallized from methanol and the crystals were collected by filtration, washed well with 1N hydrochloric acid and methanol to give (3,4,5-tris(octadecyloxy)-cyclohexyl)-methanol (2.58 g, 2.81 mmol, 93%).

$^1$H NMR(CDCl$_3$)

δ=0.88 (9H, t, J=6.9 Hz, OC$_{18}$H$_{37}$ C18-$\underline{H}$) 1.1-1.8 (101H, br, Cyclohexyl C1,2,6-$\underline{H}$, OC$_{18}$H$_{37}$ C2-17-$\underline{H}$) 3.14 (2H, m, Cyclohexyl C3,5-H) 3.35-3.57 (6H, m, 3,5-OC$_{18}$H$_{37}$ C1-H, HO—CH$_2$—) 3.67 (2H, t, J=6.8 Hz, 4-OC$_{18}$H$_{37}$ C1-$\underline{H}$) 3.90 (1H, s, Cyclohexyl C4-$\underline{H}$)

15-2: Synthesis of 2-(3,4,5-tris(octadecyloxy)-cyclohexylmethoxy)-9-fluorenone

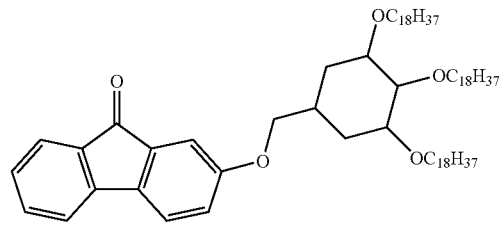

(3,4,5-Tris(octadecyloxy)-cyclohexyl)-methanol (82.5 mg, 89.7 μmol), 2-hydroxy-9-fluorenone (26.4 mg, 135 μmol) and triphenylphosphine (35.3 mg, 135 μmol) were dissolved in dehydrated THF (1.6 mL), DIED (27 μL, 137 μmol) was added, and the mixture was stirred for 1.5 hours. THF was evaporated, and 90% aqueous acetonitrile (10 mL) was added to the residue to allow crystallization. The crystals were filtered, and the obtained crystals were washed well with acetonitrile (10 mL) to give 2-(3,4,5-tris(octadecyloxy)-cyclohexylmethoxy)-9-fluorenone (91.2 mg, 83.1 μmol, 93%).

δ=0.88 (9H, t, J=6.6 Hz, OC$_{18}$H$_{37}$ C18-H) 1.1-1.9 (101H, br, Cyclohexyl C1,2,6-H, OC$_{18}$H$_{37}$ C2-17-$\underline{H}$) 3.18 (2H, m, Cyclohexyl C3,5-H) 3.38-3.56 (4H, m, 3,5-OC$_{18}$H$_{37}$ C1-$\underline{H}$) 3.68 (2H, t, J=6.6 Hz, 4-OC$_{18}$H$_{37}$ C1-$\underline{H}$) 3.87 (2H, d, J=5.7 Hz, fl-O—CH$_2$—) 3.93 (1H, s, Cyclohexyl C4-H) 6.96 (1H, dd, J=8.2, 2.4 Hz, fl C3-H) 7.20 (2H, m, fl C3,7-$\underline{H}$) 7.36-7.46 (3H, m, fl C4,5,6-$\underline{H}$) 7.60 (1H, d, J=7.2 Hz, fl C8-$\underline{H}$)

15-3: Synthesis of 9-(4-chlorophenyl)-2-(3,4,5-tris(octadecyloxy)-cyclohexylmethoxy)-9-fluorenol

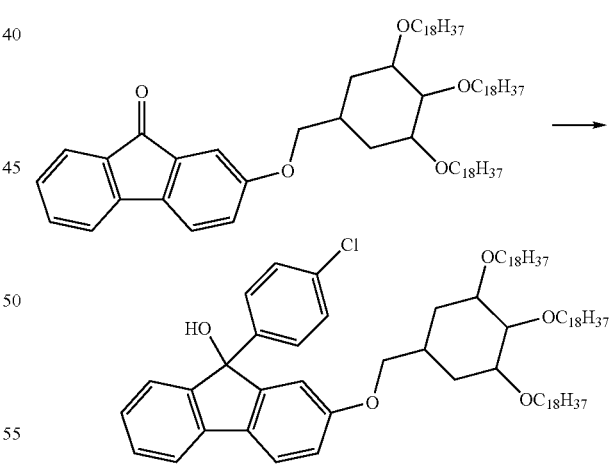

2-(3,4,5-Tris(octadecyloxy)-cyclohexylmethoxy)-9-fluorenone (61.6 mg, 56.1 μmol) was dissolved in dehydrated THF (3 mL), 4-chlorophenyl-magnesium bromide (200 μmol) was added, and the mixture was stirred at 40° C. for 3 hours. After evaporation of the solvent, 0.5N hydrochloric acid (6 mL) was added to the residue to allow crystallization. The crystals were collected by filtration, washed well with hydrochloric acid, water and methanol in this order to give 9-(4-chloro-phenyl)-2-(3,4,5-tris(octadecyloxy)-cyclohexylmethoxy)-9-fluorenol (64.1 mg, 53.0 μmol, 94%).

δ=0.88 (9H, t, J=6.7 Hz, OC$_{18}$H$_{37}$ C18-H) 1.1-1.9 (101H, br, Cyclohexyl C1,2,6-H, OC$_{18}$H$_{37}$ C2-17-H) 2.42 (1H, s, —OH) 3.15 (2H, d, J=9.8 Hz, Cyclohexyl C3,5-H) 3.45 (4H, m, 3,5-OC$_{18}$H$_{37}$ C1-H) 3.66 (2H, t, J=6.5 Hz, 4-OC$_{18}$H$_{37}$ C1-H) 3.78 (2H, d, J=5.3 Hz, fl-O—CH$_2$—) 3.91 (1H, s, Cyclohexyl C4-H) 6.80 (1H, s, fl C1-H) 6.88 (1H, d, J=8.3 Hz, fl C3-H) 7.13-7.38 (7H, m,Ph C2,3,5,6-H, fl C6,7,8-H) 7.55 (2H, m, fl C4,5-H)

15-4: Synthesis of 9-(4-chlorophenyl)-2-(3,4,5-tris(octadecyloxy)-cyclohexylmethoxy)-9-bromofluorene

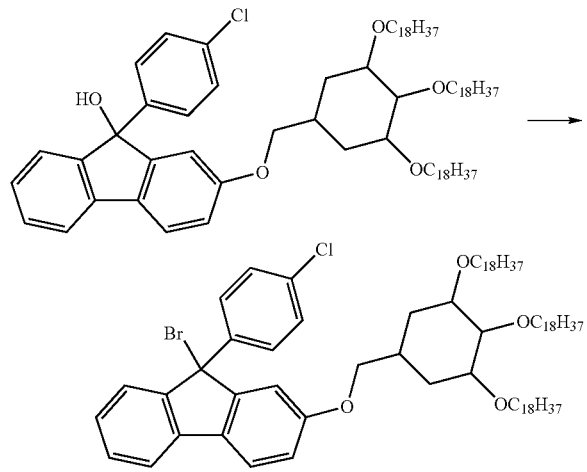

9-(4-Chlorophenyl)-2-(3,4,5-tris(octadecyloxy)-cyclohexylmethoxy)-9-fluorenol (62.0 mg, 51.2 μmol) was dissolved in chloroform (2 mL), acetyl bromide (13 μmol, 172 μmol) was added, and the mixture was stirred at room temperature for 1 hours. After evaporation of the solvent, acetonitrile was added to the residue to allow crystallization to give 9-(4-chlorophenyl)-2-(3,4,5-tris(octadecyloxy)-cyclohexylmethoxy)-9-bromofluorene (63.9 mg, 50.2 μmol, 98%). δ=0.88 (9H, t, J=6.6 Hz, OC$_{18}$H$_{37}$ C18-H) 1.1-1.9 (101H, br, Cyclohexyl C1,2,6-H, OC$_{18}$H$_{37}$ C2-17-H) 3.16 (2H, d, J=10.3 Hz, Cyclohexyl C3,5-H) 3.46 (4H, m, 3,5-OC$_{18}$H$_{37}$ C1-H) 3.68 (2H, t, J=6.7 Hz, 4-OC$_{18}$H$_{37}$ C1-H) 3.82 (2H, m, fl-O—CH$_2$—) 3.92 (1H, s, Cyclohexyl C4-H) 6.90 (1H, d, J=8.3 Hz, fl C3-H) 6.96 (1H, s, fl C1-H) 7.18-7.26 (3H, m,Ph C3,5-H, fl C7-H) 7.34 (1H, t, J=7.1 Hz, fl C6-H) 7.43 (1H, d, J=7.6 Hz, fl C8-H) 7.48 (2H, d, J=8.7 Hz, Ph C2,6-H) 7.57 (2H, m, fl C4,5-H)

Reference Example 1

Synthesis of Z-alanine-trityl anchor (3,4,5-tristearyloxy) compound

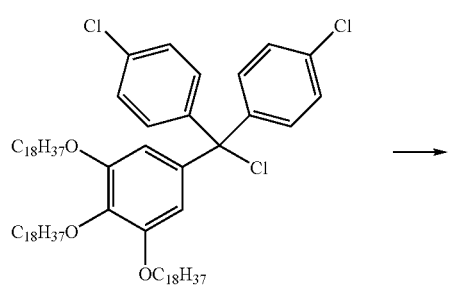

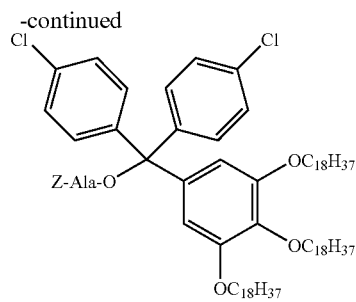

bis-(4-Chlorophenyl)-(3,4,5-tristearyloxyphenyl)-methyl chloride (150 mg, 0.13 mmol) prepared according to the method described in WO2007/122847 was dissolved in chloroform (1.5 ml), Z-alanine (58 mg, 0.26 mmol) was added, N-ethyldiisopropylamine (49 μl, 0.28 mmol) was added, and the mixture was stirred at room temperature for 1 hour. After completion of the reaction, the solvent was evaporated, and the residue was precipitated with acetonitrile (1.5 ml) to give Z-alanine-trityl anchor compound (169 mg, 0.13 mmol, 97%).

Reference Example 2

Synthesis of Z-alanine-trityl anchor (3,5-distearyloxy) compound

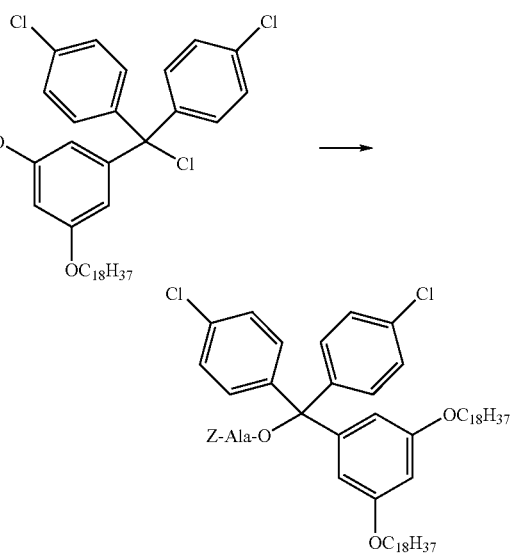

bis-(4-Chlorophenyl)-(3,5-distearyloxyphenyl)-methyl chloride (Calculated 404 mg, 0.46 mmol) prepared according to the method described in WO2007/122847 was dissolved in chloroform (4 ml), Z-alanine (204 mg, 0.91 mmol) was added, N-ethyldiisopropylamine (173 μl, 1.00 mmol) was added, and the mixture was stirred at room temperature for 3 hours. After completion of the reaction, the solvent was evaporated, and the residue was precipitated with acetonitrile (8 ml) to give Z-alanine-trityl anchor compound (548 mg, 0.51 mmol, 100% 2 steps).

Experimental Example (1) Stability Evaluation of Fluorene Type Anchor-Condensed Product and Trityl Type Anchor-Condensed Product, with Z-Alanine A Z-alanine-anchor-condensed product (35 mg) was dissolved or suspended in methanol and 10% acetic acid/chloroform solution (0.7 ml), and the amount of Z-alanine (Z-Ala-OH) liberated in a predetermined time was quantified.

The trityl type anchor showed liberation of Z-alanine in methanol even in 1 hour and the bond to the anchor was cut. On the other hand, it was confirmed that the fluorene type anchor was not cut even in methanol or under acidic conditions of 10% acetic acid solution (see Table 1).

THF and the like and scarcely dissolves in polar organic solvents. In the process of elongation of peptide chain length wherein the substance is used as a protecting group for C-terminal or side chain in the peptide synthesis and an operation including reaction in a halogen solvent, followed by precipitation with methanol and the like to remove impurity is repeated, a side reaction to yield diketopiperazine is suppressed and peptide chain can be elongated in a high yield and with high quality. Moreover, the anchor enables selective

TABLE 1

| Amount of liberated Z-Ala-OH after stirring at room temperature for 1 hr | | |
|---|---|---|
| | MeOH | 10% AcOH/CHCl$_3$ |
| 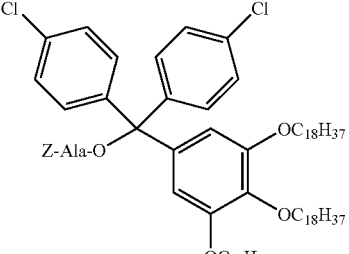 | 70% | 100% |
| 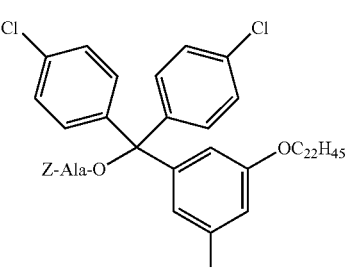 | 20% | 75% |
| 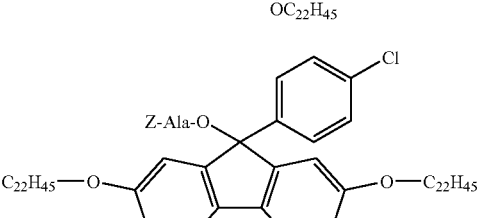 | 2% | 4% |
| 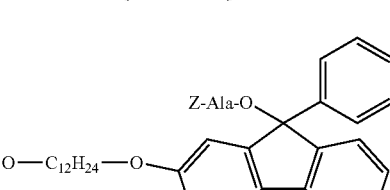 | 0% | 0% |

INDUSTRIAL APPLICABILITY

A particular compound having a fluorene skeleton provided substance which functions as a superior protecting group and anchor can be produced. The anchor can be removed under weak acidic conditions, and selectively removed even when other protecting groups (peptideside chain protecting group etc.) still remain in the compound obtained by organic synthesis reaction. Namely, the compound is a substance that enables easy precipitation in methanol and the like, since it dissolves only in halogen solvents, removal thereof while maintaining the protecting group. Using the method of the present invention, various active pharmaceutical ingredients (API), intermediates and final products are easily obtained.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

---

---

The invention claimed is:

1. A method of producing a peptide by a liquid phase synthesis process, comprising:
   (a) binding a fluorene compound to an amino acid or a peptide, to obtain a bonded product;
   (b) precipitating said bonded product and;
   (c) deprotecting said bonded product after a reaction to produce a peptide;
   wherein said fluorene compound is represented by formula (I):

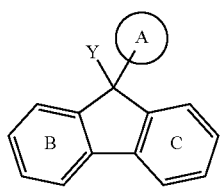

(I)

wherein ring A is an aromatic ring; Y is a group reactive with one or more groups selected from an amino group, a carboxyl group, and a mercapto group; at least one of rings A, B, and C has an organic group having an aliphatic hydrocarbon group; and rings A, B, and C each independently optionally have an electron withdrawing group.

2. A method of producing a peptide by a liquid phase synthesis process, comprising:
   (a) obtaining a C-fluorene compound-protected amino acid or a C-fluorene compound-protected peptide by condensing a fluorine compound with the C-terminal of a first N-protected amino acid or a first N-protected peptide;
   (b) removing a protecting group of the N-terminal of the amino acid or peptide obtained in the above-mentioned step to obtain an N-deprotected amino acid or peptide;
   (c) condensing the N-terminal of the N-deprotected amino acid or peptide with a second N-protected amino acid or a second N-protected peptide, to obtain a peptide; and
   (d) precipitating the peptide obtained in the above-mentioned step;
   wherein said fluorene compound is represented by formula (I):

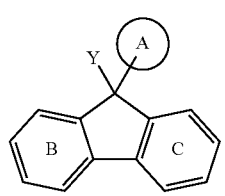

(I)

wherein ring A is an aromatic ring: Y is a group reactive with one or more groups selected from an amino group, a carboxyl group, and a mercapto group; at least one of rings A, B, and C has an organic group having an aliphatic hydrocarbon group; and rings A, B, and C each independently optionally have an electron withdrawing group.

3. The method according to claim 2, further comprising one or more repetitions of:
  (e) deprotecting the N-terminal of the peptide obtained in (d) precipitating;
  (f) condensing the N-terminal of peptide obtained in (e) deprotecting with N-protected amino acid or N-protected peptide to obtain an elongated peptide; and
  (g) precipitating the elongated peptide obtained in the above-mentioned step.

4. A method of producing a peptide further comprising, after the final precipitation step according to claim 2, a step of deprotecting the C-terminal of peptide wherein the C-terminal is protected with a fluorine compound.

* * * * *